( 12 ) United States Patent
Ogawa et al.

(10) Patent No.: US 7,682,604 B2
(45) Date of Patent: *Mar. 23, 2010

(54) COMPOSITE POWDER, COSMETICS CONTAINING THE SAME, AND PROCESS FOR PRODUCING COMPOSITE POWDER

(75) Inventors: Katsuki Ogawa, Yokohama (JP); Kyoko Joichi, Yokohama (JP); Tsuyoshi Miyamoto, Yokohama (JP); Tetsuya Kanemaru, Yokohama (JP); Katsuhiko Yagi, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 1544 days.

This patent is subject to a terminal disclaimer.

(21) Appl. No.: 10/507,007

(22) PCT Filed: Mar. 7, 2003

(86) PCT No.: PCT/JP03/02712

§ 371 (c)(1),
(2), (4) Date: Sep. 7, 2004

(87) PCT Pub. No.: WO03/074012

PCT Pub. Date: Sep. 12, 2003

(65) Prior Publication Data

US 2005/0158257 A1    Jul. 21, 2005

(30) Foreign Application Priority Data

Mar. 7, 2002  (JP) ............................... 2002-062653
Mar. 7, 2002  (JP) ............................... 2002-062748

(51) Int. Cl.
*A61K 7/021*    (2006.01)

(52) U.S. Cl. ........................................................ 424/63
(58) Field of Classification Search ................... 424/63
See application file for complete search history.

(56) References Cited

U.S. PATENT DOCUMENTS

| 4,603,047 | A | | 7/1986 | Watanabe et al. |
| 4,956,019 | A | * | 9/1990 | Noguchi et al. ............. 106/415 |
| 5,380,360 | A | | 1/1995 | Noguchi et al. |
| 6,086,666 | A | | 7/2000 | Noguchi et al. |
| 2004/0126320 | A1 | * | 7/2004 | Miyamoto et al. ......... 424/9.41 |
| 2007/0253989 | A1 | * | 11/2007 | Abe et al. ................... 424/401 |

OTHER PUBLICATIONS

Japanese Patent Abstract, Publication No. 07-003181, Published Jan. 6, 1995 "Flesh-Colored Sintered Pigment And Flesh-Colored Makeup Cosmetic Containing The Same".
Japanese Patent Abstract, Publication No. 08-283124, Published Oct. 29, 1996 "Cosmetic".
Japanese Patent Abstract, Publication No. 11-021468, Published Jan. 26, 1999 "Ultraviolet-Screening Pigment".

* cited by examiner

*Primary Examiner*—Robert A Wax
*Assistant Examiner*—Aradhana Sasan
(74) *Attorney, Agent, or Firm*—Rankin, Hill & Clark LLP

(57) ABSTRACT

An object of the present invention is to provide a composite powder, cosmetics containing the same, and the production method of the same. When blended into cosmetics, the above-described composite powder corrects skin surface unevenness and imperfections in skin color, renders a natural finish, and have durability in finished makeup. In order to achieve the above-mentioned object, the composite powder of the present invention comprises flaky substrate powder and barium sulfate particles or zinc oxide particles that adhere to the surface, in protrusions, of the substrate powder.

20 Claims, 26 Drawing Sheets

Example 1

(A)

(B)

Example 5

Example 7

Example 10

Example 11

Example 12

Example 13

Example 18

Example 19

Example 20

Example 21

Example 22

Example 52

Example 53

Example 54

Example 55

Example 56

Example 60

Example 61

Example 62

Example 65

Example 66

Example 67

COMPOSITE POWDER, COSMETICS CONTAINING THE SAME, AND PROCESS FOR PRODUCING COMPOSITE POWDER

RELATED APPLICATIONS

This application claims the priority of Japanese Patent Application No. 2002-62653 filed on Mar. 7, 2002 and Japanese Patent Application No. 2002-62748 filed on Mar. 7, 2002, which are incorporated herein by reference.

TECHNICAL FIELD

The present invention relates to composite powder, cosmetics containing the same, and the production method of the same, and in particular, relates to the correction of skin surface unevenness, the correction of imperfections in skin color, natural finish, and also the improvement in durability of finished makeup.

BACKGROUND ART

In the past, as a method to uniformly correct the unevenness of the skin, such as prominence of pores and fine wrinkles, the blurring effect due to diffuse reflection with spherical powder has been used.

Especially lately, in order to achieve such an effect, spherical resin powders with a low refractive index, such as PMMA and nylon, and spherical inorganic powders with a refractive index of approximately 1.5-2.0, such as barium sulfate and alumina, have been used. In addition, composite powders with increased diffuse reflection prepared by uniformly attaching spherical resin powder on the surface of flaky powder such as talc, mica, alumina, or barium sulfate, are being developed. Composite powders with the increased blurring effect, which is achieved with the improved light diffusion due to the increased refractive index by forming a titanium oxide layer and a silica layer on the surface of spherical silica particles, have also been developed.

On the other hand, titanium oxide pigment with a refractive index of 2.69, which has good hiding power and coloring ability, has been used to correct imperfections in skin color, such as dullness, blotches, freckles, redness, and dark rings around the eyes.

The correction based on the spectral characteristics of the powder is also effective as a method to correct imperfections in skin color.

The blurring effect based on the diffuse reflection of spherical powder can correct skin surface unevenness such as prominence of pores and fine wrinkles. Thus, it is satisfactory from the standpoint of uniformly made-up skin. However, the blurring effect does not sufficiently correct imperfections in skin color.

A composite powder, in which the surface of flaky powder is uniformly covered with fine spherical resin powder, produces a strong gloss since the fine resin powder of less than 0.5 μm with precise arrangement in adhesion functions as a plane and causes normal surface reflection. In addition, since the refractive index of the resin powder is less than 1.5, the resin powder will mix with oil components in cosmetics and become transparent. Thus, expected diffuse reflection is not realized, and skin surface unevenness will become more conspicuous. Therefore, it is not satisfactory from the standpoint of uniformly made-up skin.

On the other hand, it is possible to hide imperfections in skin color by using a titanium oxide pigment with a high refractive index (2.69). However, its tone is matte without gloss, and the finished makeup foundation is pale because of strong light scattering due to the high refractive index. Thus, a natural finish can never be achieved. In addition, the hiding power is too strong to give clearness, and it produces only an unnatural impression compared with the actual skin.

In order to solve this problem, a powder containing titanium oxide doped with iron oxide was developed; thus, the make-up adapted to natural skin color was targeted by coloring with yellow orange pigment (Japanese Unexamined Patent Publication No. H07-3181). Although this powder made a certain contribution to a natural finish, the problem was not satisfactorily solved.

The composite powder, in which a substrate powder is covered with barium sulfate particles, was also developed (Japanese Examined Patent Publication No. H02-42388, Japanese Examined Patent Publication No. H02-42387, and Patent Publication No. 3184608). However, the diffuse reflection was low, and the correction of skin surface unevenness was poor; thus, the problem was not satisfactorily solved.

In addition, the powder development based on the structure of the skin tissue has been conducted to achieve the make-up finish close to the actual skin. However, there is a limit in imitating the complicated skin tissue, thus, not only a natural finish could not be achieved, but also the hiding power turned out to be low. Therefore, imperfections in skin color such as dullness and color irregularity could not be corrected, thus, satisfactory effects cannot be expected at the present stage.

In order to correct skin surface unevenness and imperfections in skin color, natural corrections based on the diffuse reflection and spectral characteristics of powder are most effective. Actually, the correction by combining substrate particles such as interference titanated mica and composite particles with good diffuse reflection is considered effective for makeup cosmetics. Since titanated mica has a strong surface reflection, the made-up skin has a glare. Thus, skin surface unevenness due to pores and fine wrinkles are conspicuous, and it is very difficult to achieve a natural beautiful finish.

DISCLOSURE OF THE INVENTION

The present invention has been made in consideration of the above-described prior art. An object of the present invention is to provide a composite powder that, when blended in cosmetics, corrects skin surface unevenness and imperfections in skin color, achieves a natural finish, and also has durability in the finished makeup, and to provide cosmetics containing the composite powder and the production method of the composite powder.

The present inventors have diligently researched in consideration of the above problem. As a result, the inventors have found that skin surface unevenness can be corrected to a natural finish, and the finished makeup can be long lasting in the following case. That is when a fixed amount of protruding barium sulfate particles or zinc oxide particles adhere to the surface of flaky substrate particles, and an obtained composite powder is blended into cosmetics. The inventors have also found that skin surface unevenness and imperfections in skin color can be corrected, and a natural finish with clearness similar to optical characteristics of the skin can be achieved in the following case. That is when a fixed amount of protruding zinc oxide particles adhere to the surface of the interference titanated mica, which are flaky substrate particles, and the obtained composite powder is blended into cosmetics. These have lead to the completion of the present invention.

Namely, a composite powder according to present invention comprises a flaky substrate powder and barium sulfate particles or zinc oxide particles that adhere, in protrusions, to the surface of said substrate powder. It is also preferable that the composite powder according to present invention wherein said substrate powder generates interference colors. It is also preferable that the composite powder according to present invention wherein said substrate powder is titanated mica. It is also preferable that the composite powder according to present invention wherein barium sulfate particles or zinc oxide particles, which adhere to the surface of said substrate powder, have approximately uniform particle diameters. It is also preferable that the composite powder according to present invention wherein said barium sulfate particles or zinc oxide particles adhere to the surface of said substrate powder so that the distance between the particles is approximately uniform. It is also preferable that the composite powder according to present invention wherein the adhesion rate of barium sulfate particles or zinc oxide particles to said substrate is 15-100 weight %.

It is also preferable that the composite powder according to present invention wherein particles adhering to the surface of said substrate are barium sulfate particles. It is also preferable that the composite powder according to present invention wherein the coverage with barium sulfate particles is 10-70% with respect to the surface area of said substrate powder. It is also preferable that the composite powder according to present invention wherein said barium sulfate particles are flaky, and said barium sulfate particles adhere to the surface of the substrate powder by contacting at the peripheral points of the flakes and adhere at a certain angle with respect to the surface of the substrate powder. It is also preferable that the composite powder according to present invention wherein said barium sulfate particles are approximately square flakes, and said barium sulfate particles adhere to the surface of the substrate powder by contacting at the peripheral points of the flakes and adhere at a certain angle with respect to the surface of the substrate powder. It is also preferable that the composite powder according to present invention wherein said barium sulfate particles are spherical, and the number average particle diameter of said particles is 0.5-5.0 µm.

It is also preferable that the composite powder according to present invention wherein particles adhering to the surface of said substrate are zinc oxide particles. It is also preferable that the composite powder according to present invention wherein the coverage with zinc oxide particles is 40-90% with respect to the surface area of said substrate powder. It is also preferable that the composite powder according to present invention wherein said zinc oxide particles are long needle-shape.

A cosmetics according to present invention contains said composite powder.

A method of producing composite powder according to present invention contains adhering barium sulfate particles, wherein seed particles are allowed to coexist in a slurry solution of the flaky substrate powder, barium sulfate crystals are grown from said seed particles, which act as nuclei, by adding a barium ion solution and a sulfate ion solution to said solution and reacting them, and the formed barium sulfate particles are allowed to adhere to the surface of said substrate powder.

A method of producing composite powder according to present invention contains adhering zinc oxide particles, wherein seed particles are allowed to coexist in a slurry solution of the flaky substrate powder, zinc oxide crystals are grown from said seed particles, which act as nuclei, by adding a zinc ion solution and an alkali aqueous solution to said solution and reacting them, and the formed zinc oxide particles are allowed to adhere to the surface of said substrate powder.

It is also preferable that the method of producing composite powder according to present invention wherein the amount of the added seed particles is 0.1-15 weight % with respect to that of the substrate powder. It is also preferable that the method of producing composite powder according to present invention wherein the reaction is conducted under the conditions that the pH of the slurry solution is always adjusted in a range of 7-9.

It is also preferable that the method of producing composite powder containing adhering barium sulfate particles according to present invention wherein one or more complexing agent is allowed to coexist in the slurry solution. It is also preferable that the method of producing composite powder containing adhering barium sulfate particles according to present invention wherein the amount of added complexing agent is 0.4-10.0 equivalents with respect to that of the barium ion.

BEST MODE FOR CARRYING OUT THE INVENTION

In the following, the preferable embodiments of the present invention are explained.

The powder obtained by the production method of the present invention is a composite powder, wherein a fixed amount of protruding barium sulfate particles or zinc oxide particles adhere to the surface of the flaky powder, which acts as the substrate. When this powder is blended in cosmetics, skin surface unevenness is uniformly corrected, and a natural beautiful finish is achieved by the diffused light caused by protruded barium sulfate particles or zinc oxide particles that adhere to the surface of the flaky powder.

Barium sulfate particles or zinc oxide particles adhere in protrusions to the surface of the substrate powder. Therefore, there are less contact points between the powder and the skin, resulting in a feeling of light touch upon application. When the powder is blended in cosmetics, it produces an excellent fit feeling upon application since they are plate-shaped. In addition, it can be smoothly and uniformly spread on the skin, thus a desirable feeling of touch can be generated.

Furthermore, when zinc oxide particles are adhered, zinc oxide particles absorb sebum, which is secreted over time. Thus, the optical property is maintained for a long time, and a long-lasting make-up can be achieved without an undesirable gloss and makeup deterioration that could be caused by sebum.

The above-described "protruding" barium sulfate particles can be obtained in various shapes depending upon used substrate powders and production conditions. Normally, as an example shown in FIG. 1, flaky particles described below are obtained. The particles adhere to the surface of the substrate powder by contacting at the peripheral points of the flakes, and they adhere to the surface of the substrate powder at a certain angle with respect to the surface.

Figure 11:
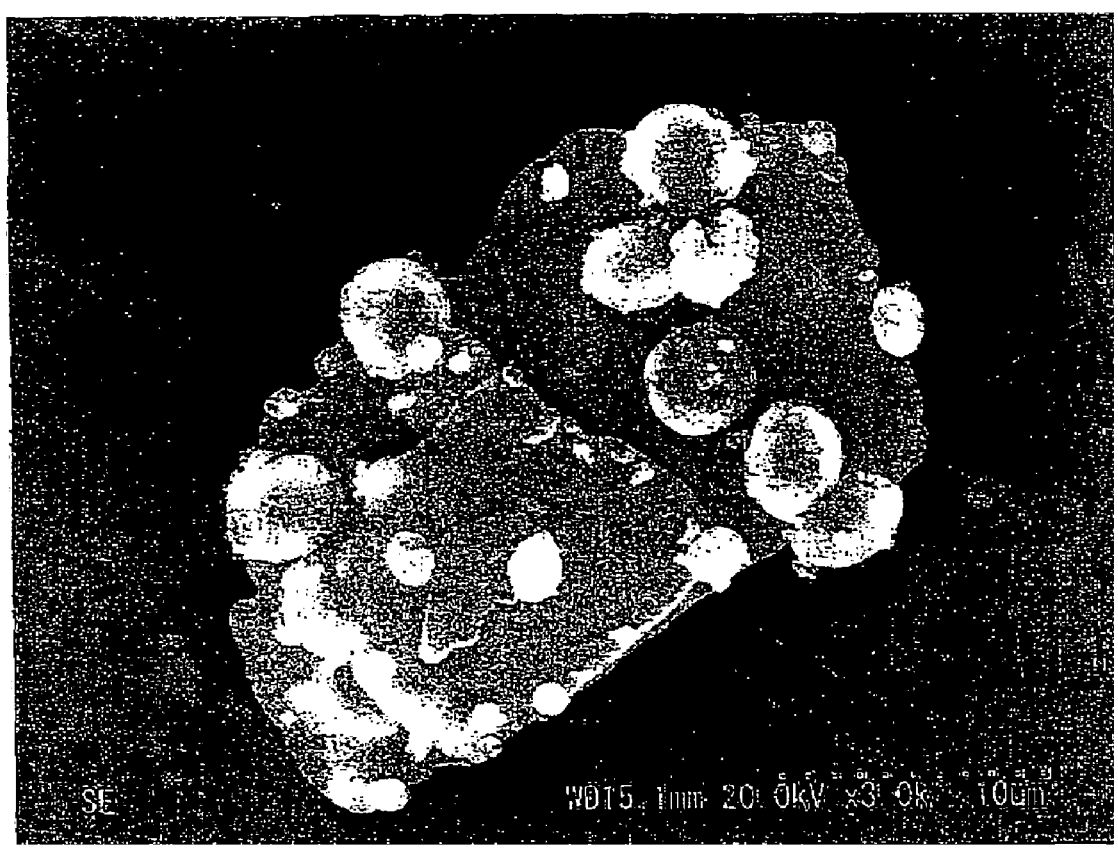
FIG. 11 shows an SEM picture of surface of a composite powder of Example 18.

It is also possible, as an example shown in FIG. 11, to allow barium sulfate particles on the substrate powder to be spherical. This can be achieved by including a complexing agent in the reaction solution during production.

Likewise, the above-described "protruding" zinc oxide particles can be obtained in various shapes depending upon used substrate powders and production conditions. Normally, as an example shown in FIG. 16, thin long needle-shape can be obtained.

Examples of the flaky powder that is used as the substrate of a composite powder include mica, talc, sericite, kaolin, titanium oxide, silica, alumina, iron oxide, boron nitride, synthetic mica, synthetic talc, hydroxyapatite, barium sulfate, zinc oxide, etc. As far as the weight average particle diameter (equivalent spherical diameter) is 1-150 μm, there is no particular limitation.

It is preferable that the adherence rate of barium sulfate or zinc oxide on the substrate powder is 15-100 weight %.

It is preferable that the coverage with barium sulfate particles is 10-70% with respect to the surface area of substrate powder. It is preferable that the coverage with zinc oxide particles is 40-90% with respect to the surface area of substrate powder.

According to the present invention, a composite powder is obtained by attaching a fixed amount of protruding barium sulfate particles or zinc oxide particles on the surface of a flaky substrate powder, such as titanated mica etc., which can generate interference colors. The obtained composite powder is blended into cosmetics, and in particular, into makeup cosmetics. Thus, it is possible to uniformly correct skin surface unevenness and imperfections in skin color based on the spectral characteristics due to interference colors, which are generated by the flaky powder, and the light diffusion due to barium sulfate particles or zinc oxide particles adhering to the surface of the flaky powder in protrusions.

In addition, since the diffuse reflection due to the powder increases by attaching barium sulfate particles or zinc oxide particles in protrusions, the strong surface reflection unique to titanated mica etc. can be reduced.

Furthermore, when barium sulfate particles are attached to the powder, it is possible to achieve a natural beautiful finish with a feeling of clearness since the refractive index of barium sulfate (1.64) is relatively close to the refractive index of the skin (1.56).

When zinc oxide particles are attached to the powder, a natural beautiful finish with moderate gloss is possible, even when blended into an emulsion base, since the refractive index of zinc oxide (2.05) is higher than the refractive index of oil (1.4-1.5).

More specifically, the interference lights from the layer-structure powder such as titanated mica, which generates interference colors, are blue, yellow, green, red, violet, etc. The selection of the suitable interference colors corresponding to the skin can correct imperfections in skin color and can achieve a natural beautiful finish without glare, which is unique to titanated mica etc.

For example, dull skin and dark rings around the eyes can be corrected with a red to orange reflected interference light since yellow to red light, which is absorbed by melanin and congestion, is lacking. Thus, a healthy bright skin makeup with a feeling of clearness can be achieved.

Skin with strong red tint, such as sensitive skin and atopic skin, cases of which have lately increased, and the acne skin are lacking green color that is absorbed by hemoglobin pigment in the blood. This can be corrected by green reflected interference light, and a natural finish with decreased red tint can be achieved. In the case of skin that has color non-uniformity, such as blotches and freckles, yellow color is absorbed by dark melanin pigment. This can be corrected by yellow reflected interference light, and natural, uniform, beautifully made-up skin can be achieved.

Examples of the flaky powder that is used as the substrate for a powder with layered structure, which generates interference colors, include titanated mica, mica covered by titanium oxide of the low-oxidation state, titanated mica covered with iron oxide. As far as the weight average particle diameter (equivalent spherical diameter) is 1-150 μm, there is no particular limitation.

It is preferable that the adherence rate of barium sulfate or zinc oxide on the surface of the substrate powder is 15-100 weight % with respect to the substrate, which generates interference colors. If the adherence rate of barium sulfate or zinc oxide is equal or less than 15 weight %, it is difficult to suppress surface reflection from the flaky substrate powder and an undesirable glare is observed. If zinc oxide is attached on the substrate, the adsorption of sebum will become poor over time and an undesirable gloss will show up on the made-up skin. On the other hand, if the adherence rate exceeds 100 weight %, a rough texture is generated on the powder and a feeling of touch upon application will become extremely poor. In addition, the interference colors from the flaky powder will be concealed excessively, the color correction of the skin will be disturbed, and the makeup's effect will drastically deteriorate. It is more preferable that the adherence rate of barium sulfate or zinc oxide is 40-70 weight %.

It is preferable that the coverage rate of the substrate surface with barium sulfate particles is 10-70% with respect to the total surface area of the substrate powder. It is also preferable that the coverage rate of the substrate surface with zinc oxide particles is 40-90% with respect to the total surface area of the substrate powder. If the coverage rate with barium sulfate or zinc oxide exceeds the above-mentioned upper limit, interference colors by the flaky powder will be concealed excessively, and the normal reflection will disappear. Thus, the color correction of the skin may be disturbed, leading to an undesirable situation. If the coverage rate is less than the above-mentioned lower limit, the number of the cover particles is too small and the diffusion effect cannot be achieved. As a result, the surface reflection by the flaky substrate powder cannot be suppressed, and a glare may show up.

Figure 1:
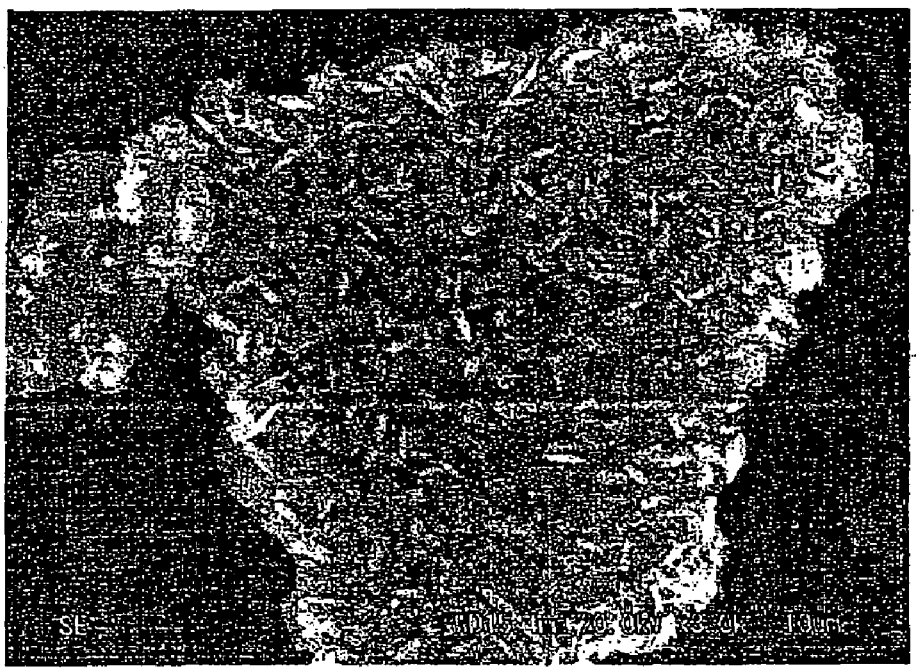
FIG. 1 shows an SEM picture of surface of a composite powder of Example 1.
Figure 1:

A composite powder was prepared according to the production method of the present invention using barium sulfate as adhering particles and titanated mica as a substrate. An SEM picture of the surface of the obtained composite powder is shown in FIG. 1. The surface structure shows that barium sulfate particles, which are approximately square, adhere to the surface of the substrate powder by contacting at the peripheral points of the flakes, and they adhere to the surface of the substrate powder at a certain angle with respect to the surface. In addition, barium sulfate particles adhere to the surface of the substrate powder so that the distances between the particles are approximately the same. This structure of adherence is unique to the case that titanated mica is used as a substrate.

According to the production method of the present invention, in order to obtain flaky powder to which protruding particles adhere, seed particles are used during the powder production. For example, when barium sulfate is attached during the reaction by mixing barium ion solution and sulfate ion solution, and when zinc oxide is attached during the reaction by mixing zinc ion solution and alkali ion aqueous solution, fine particles of metal oxides are allowed to coexist as seed particles. In this way, the seed particles act as the nuclei for the crystal growth of barium sulfate or zinc oxide. Thus, crystals of barium sulfate or zinc oxide grow from the seed particles to complete a structure in which formed particles adhere to the substrate powder. The production method of composite powder according to the present invention is explained below.

Initially, a production method of composite powder in which barium sulfate is attached is explained.

A barium compound that is used as a raw material for the production of composite powder can be any compound as far as barium ions can be generated in a solvent such as water or alcohol, and there is no particular limitation.

As examples of barium compounds, there are barium hydroxide, barium chloride, barium sulfide, barium nitrate, barium acetate, etc. Among these, barium chloride and barium hydroxide are preferable since the treatment of by-products are easy.

A sulfate compound that is used as a raw material for the production of composite powder can be any compound as far as sulfate ions can be generated in a solvent such as water or alcohol, and there is no particular limitation.

As examples of sulfate compounds, there are sulfuric acid, sodium sulfate, sodium hydrogensulfate, ammonium sulfate, potassium sulfate, lithium sulfate, etc. Among these, sulfuric acid, sodium sulfate, and ammonium sulfate are especially preferable.

When a barium compound and a sulfate compound are reacted, barium ion solution and sulfate ion solution are prepared in advance by dissolving a barium compound and a sulfate compound in water or alcohol, separately. More dilute, during the reaction, the concentration of barium ion and the concentration of sulfate ion, the better the feeling of touch by formed barium sulfate upon cosmetic application.

A barium ion solution and a sulfate ion solution are usually prepared in a concentration of 0.01 mmol/L-1 mol/L. Preferably the concentration should be in a range of 1 mmol/L-100 mmol/L. If the concentration is smaller than this range, the efficiency in the industrial production will be poor. If the concentration is higher than this range, the generation of nuclei is high because of super saturation. Therefore, many fine particles are produced and the aggregation will take place. As a result, they are not useful for cosmetic application.

If a barium ion solution and a sulfate ion solution are mixed over time during the reaction, the reaction in the solution proceeds at a lower concentration than the actual concentration at the preparation of the solutions.

From the standpoint of crystal growth of barium sulfate particles, it is preferable to carry out the reaction by always adjusting the pH in a range of 7-9.

As seed particles to be added to the reaction, there are particles of titanium oxide, zinc oxide, alumina, aluminum hydroxide, silica, iron oxide, barium sulfate, etc. The weight average particle diameter (equivalent spherical diameter) of these particles should be 0.02-2 μm and preferably 0.1-0.5 μm. These fine particles will become nuclei for the crystal growth of barium sulfate, and they promote the adherence of barium sulfate to the substrate powder surface.

The seed particles are added in a range of 0.1-15 weight % with respect to the substrate powder. If it is less than 0.1 weight %, the control of the particle diameter and adhesion structure for the formed barium sulfate particles will become difficult, and the expected diffuse reflection characteristics may not obtained. If it exceeds 15 weight %, the number of nuclei for crystal growth becomes too numerous, and the control of morphology tends to become difficult. In addition, the interference colors from flaky powder are excessively concealed, and color correction of the skin may be disturbed, leading to an undesirable situation. The more preferable amount of the seed particles, to be added, is 1-10 weight % with respect to the substrate powder.

In addition, it is possible to control the shape of barium sulfate particles to be spherical by adding an appropriate amount of a complexing agent into the reaction solution.

A composite powder was prepared using barium sulfate as adhering particles and titanated mica as a substrate with the coexistence of sodium L-glutamate during the reaction. An SEM picture of the surface of the obtained composite powder is shown in FIG. 11. The surface structure shows that barium sulfate particles, which are spherical, adhere to the surface of the substrate powder. This structure was unique to the case in that a complexing agent was allowed to coexist.

Figure 29:
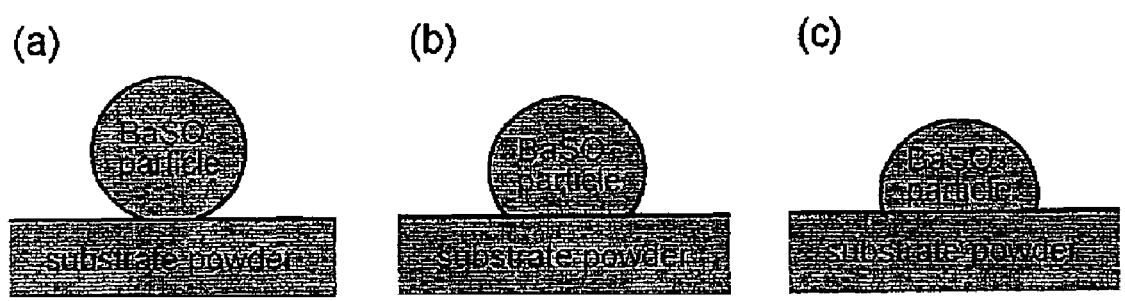
FIG. 29 shows an explanation drawing for a composite powder containing adhering spherical barium sulfate particle of the present invention.

Generally speaking, "spherical" particles represent particles that are approximately circular when viewed under the projection from all angles. However, "spherical" barium sulfate particles of the present invention include particles that are approximately circular to approximately semi-circular when viewed under the projection from the side of the particle adhering plane as shown in FIG. 29(a)-FIG. 29(c).

When the barium sulfate particles adhering to the surface of substrate powder are spherical, it is preferable that the number average particle diameter is 0.5-5.0 μm. If the average particle diameter is less than 0.5 μm, most light is allowed to transmit and the diffusion characteristics may not be sufficiently achieved. On the other hand, if the average particle diameter exceeds 5.0 μm, the interference colors of substrate powder are excessively concealed and color correction of the skin may be disturbed, leading to an undesirable situation. It is more preferable that the average particle diameter of the spherical barium sulfate particles is 1.0-3.0 μm.

It is preferable that one or more complexing agent is allowed to coexist in the reaction solution in the composite powder production according to the present invention. As examples of complexing agents, there are L-glutamic acid, aspartic acid, succinic acid, citric acid, tartaric acid, hydroxy-carboxylic acids, ethylenediaminetetraacetic acid (EDTA), nitrilotriacetic acid (NTA), etc; in addition, salts of these compounds may be used. Among these complexing agents, sodium glutamate and sodium aspartate are particularly preferable.

When barium sulfate particles are controlled to be spherical, a complexing agent should be added in a range of 0.4-10.0 equivalents with respect to the barium ion. If it is less than 0.4 equivalents, it is difficult to control the adhering particles to be spherical. If it exceeds 10.0 equivalents, formed barium sulfate will aggregate and the uniform adhesion to the substrate cannot be achieved, leading to aggregation. As a result, the feeling of touch upon application is lowered, and they are not useful for cosmetic application. It is more preferable that the amount of complexing agent to be added is 1.0-5.0 equivalents with respect to the barium ion.

In order to control the crystal g/growth of particles, metal ions may be added. By controlling the crystal growth of particles, the diffuse reflection can be enhanced, or the angle-dependent gloss can be rendered. When titanated mica is used as a substrate, the addition of a metal ion may induce the growth of crystals of a different morphology rather than the above-mentioned quasi-square flakes.

Examples of metal ions include lithium ion, sodium ion, potassium ion, magnesium ion, calcium ion, and aluminum ion. They can be used alone or by the combination of more than one species. Respective metal ions are provided as an aqueous solution or an alcohol solution of the salt containing the corresponding metal.

The metal ion should be added in a range of 0.01-10 equivalents with respect to the barium ion. If it is less than 0.01 equivalents, it is difficult to control the morphology of the adhesion structure. If it exceeds 10 equivalents, the formed barium sulfate will aggregate and the uniform adhesion to the substrate cannot be achieved. As a result, the feeling of touch upon application is poor; thus, the aggregated barium sulfate is not useful for the cosmetic application.

Examples of metal salts that provide corresponding metal ions include lithium salts such as lithium hydroxide, lithium chloride, lithium nitrate, lithium carbonate, and lithium acetate; sodium salts such as sodium hydroxide, sodium chloride, sodium nitrate, sodium carbonate, and sodium acetate; potassium salts such as potassium hydroxide, potassium chloride, potassium nitrate, potassium carbonate, and potassium acetate; magnesium salts such as magnesium hydroxide, magnesium chloride, magnesium nitrate, magnesium carbonate, and magnesium acetate; calcium salts such as calcium hydroxide, calcium chloride, calcium nitrate, calcium carbonate, and calcium acetate; and aluminum salts such as aluminum hydroxide, aluminum chloride, aluminum nitrate, aluminum carbonate, and aluminum acetate.

Except for these metal ions, for the control of crystal growth of particles, one or more water-soluble organic compound may be allowed to coexist in the reaction solution. As examples of these water-soluble organic compounds, there are lower alcohols with 1-4 carbons, such as methanol, ethanol, n-propyl alcohol, isopropyl alcohol; and water-soluble organic polymers such as polyethylene glycols with the molecular weight of 400-20000, and polyacrylamides such as poly(N,N-diethylacrylamide) and poly(N-isopropylacrylamide).

In order to carry out a reaction, a solution of the barium ion and a solution of the sulfate ion, which are prepared as described above, are added to a slurry of the substrate powder containing seed particles, metal ions, and acids, as necessary. After the reaction, a composite powder of the present invention is obtained through the treatments of filtering, washing with water, and powdering.

Representative embodiments according to the present invention are described below for the production method of composite powder with adhering barium sulfate.

Embodiment 1

A solution prepared by ultrasonic dispersion of alumina fine particles, which were used as seed particles, was added to a slurry of titanated mica. After the mixture is stirred, to this were simultaneously added a barium ion solution and a sulfate ion solution that were prepared as described above. On this occasion, the mole ratio of the sulfate ion and the barium ion was set in a range of 1/2-2/1. The reaction temperature was set preferably at 0-90° C., more preferably at 10-60° C., and further more preferably at 20-40° C. It is preferable to always adjust the pH of the slurry in a range of 7-9 during the reaction.

Embodiment 2

A solution prepared by ultrasonic dispersion of silica fine particles, which were used as seed particles, was added to a slurry of titanated mica. After the mixture is stirred, to this was added a solution of a metal salt containing the specific metal ion. To the prepared slurry were simultaneously added a barium ion solution and a sulfate ion solution that were prepared as described above. On this occasion, the mole ratio of the sulfate ion and the barium ion was set in a range of 1/2-2/1. The reaction temperature was set preferably at 0-90° C., more preferably at 10-60° C., and further more preferably at 20-40° C. It is preferable to always adjust the pH of the slurry in a range of 7-9 during the reaction.

Embodiment 3

A solution prepared by ultrasonic dispersion of alumina fine particles, which were used as seed particles, was added to a slurry of titanated mica, and the mixture is stirred. After sodium L-glutamate, which is a complexing agent, was added in an amount of 0.8-5 equivalents with respect to the barium ion, to the mixture were simultaneously added a barium ion solution and a sulfate ion solution that were prepared as described above. On this occasion, the mole ratio of the sulfate ion and the barium ion was set in a range of 1/2-2/1. The reaction temperature was set preferably at 0-90° C., more preferably at 10-60° C., and further more preferably at 20-40° C. It is preferable to always adjust the pH of the slurry in a range of 7-9 during the reaction.

The production method of composite powder that has adhering zinc oxide is explained below.

A zinc compound that is used as a raw material for the production of composite powder can be any compound as far as zinc ions can be generated in a solvent such as water or alcohol, and there is no particular limitation. For the reaction, a zinc ion solution that is prepared in advance by dissolving a zinc compound is used.

Examples of zinc compounds include inorganic salts such as zinc chloride, zinc sulfate, zinc nitrate, zinc phosphate, zinc halide, and organic salts such as zinc formate, zinc acetate, zinc propionate, zinc lactate, zinc oxalate, and zinc citrate. Among these, zinc chloride and zinc acetate are preferable since the treatment of by-products are easy Examples of raw materials for the alkali aqueous solution include lithium hydroxide, sodium hydroxide, potassium hydroxide, lithium carbonate, sodium carbonate, potassium carbonate, sodium hydrogencarbonate, potassium hydrogencarbonate, ammonia, ammonium carbonate, etc. Among these, sodium hydroxide is particularly preferable.

A zinc ion solution and an alkali aqueous solution are usually prepared in a concentration of 0.01 mmol/L-1 mol/L. Preferably the concentration should be in a range of 1 mmol/L-100 mmol/L. If the concentration is smaller than this range, the efficiency in the industrial production will be poor. If the concentration is higher than this range, the generation of nuclei is high because of super saturation. Therefore, many fine particles are produced and the aggregation will take place. As a result, they are not useful for the cosmetic application.

If a zinc ion solution and an alkali aqueous solution are mixed over time during the reaction, the reaction in the solution proceeds at a lower concentration than the actual concentration at the preparation of the solutions.

From the standpoint of crystal growth of zinc oxide particles, it is preferable to carry out the reaction by always adjusting the pH in a range of 7-9.

As seed particles to be added to the reaction, there are particles of titanium oxide, zinc oxide, alumina, aluminum hydroxide, silica, iron oxide, etc. The particle diameter of these particles should be 0.02-2 µm and preferably 0.1-0.5 µm. These fine particles will become nuclei for the crystal growth of zinc oxide, and they promote the adherence of zinc oxide to the substrate powder surface.

The seed particles are added in a range of 0.1-15 weight % with respect to the substrate powder. If it is less than 0.1 weight %, the control of the particle diameter and adhesion structure for the formed zinc oxide particles will become difficult, and the expected diffuse reflection characteristics may not obtained. If it exceeds 15 weight %, the number of nuclei for crystal growth becomes too many, and the control of morphology tends to become difficult. In addition, the interference colors from the flaky powder are excessively concealed, and color correction of the skin may be disturbed, leading to an undesirable situation. The more preferable amount of the seed particles, to be added, is 1-10 weight % with respect to the substrate powder.

In order to control the crystal growth of particles, metal ions may be added. By controlling the crystal growth of particles, the diffuse reflection can be enhanced, or the angle-dependent gloss can be rendered.

Examples of metal ions include lithium ion, sodium ion, potassium ion, magnesium ion, calcium ion, and aluminum ion. They can be used alone or by the combination of more than one species. Respective metal ions are provided as an aqueous solution or an alcohol solution of the salt containing the corresponding metal.

The metal ion should be added in a range of 0.01-10 equivalents with respect to the zinc ion. If it is less than 0.01 equivalents, it is difficult to control the morphology of the adhesion structure. If it exceeds 10 equivalents, the formed zinc oxide will aggregate and the uniform adhesion to the substrate cannot be achieved. As a result, the feeling of touch upon application is poor; thus, the aggregated zinc oxide is not useful for cosmetic application.

Examples of metal salts that provide corresponding metal ions include lithium salts such as lithium hydroxide, lithium chloride, lithium nitrate, lithium carbonate, and lithium acetate; sodium salts such as sodium hydroxide, sodium chloride, sodium nitrate, sodium carbonate, and sodium acetate; potassium salts such as potassium hydroxide, potassium chloride, potassium nitrate, potassium carbonate, and potassium acetate; magnesium salts such as magnesium hydroxide, magnesium chloride, magnesium nitrate, magnesium carbonate, and magnesium acetate; calcium salts such as calcium hydroxide, calcium chloride, calcium nitrate, calcium carbonate, and calcium acetate; and aluminum salts such as aluminum hydroxide, aluminum chloride, aluminum nitrate, aluminum carbonate, and aluminum acetate.

Except for these metal ions, for the control of crystal growth of particles, one or more water-soluble organic compound may be allowed to coexist in the reaction solution. As examples of these water-soluble organic compounds, there are organic acids such as low molecular weight carboxylic acids with 1-5 carbons, such as formic acid, acetic acid, propionic acid, butyric acid, and valeric acid; and acidic amino acids such as glutamic acid and aspartic acid; lower alcohols with 1-4 carbons, such as methanol, ethanol, n-propyl alcohol, isopropyl alcohol; and water-soluble organic polymers such as polyethylene glycols with the molecular weight of 400-20000, and polyacrylamides such as poly(N, N-diethylacrylamide) and poly(N-isopropylacrylamide).

In order to carry out a reaction, a solution of the zinc ion and an aqueous solution of the alkali ion, which are prepared as described above, are added to a slurry of the substrate powder containing seed particles, metal ions, and acids, as necessary. After the reaction, a composite powder of the present invention is obtained through the treatments of filtering, washing with water, and powdering.

Representative embodiments according to the present invention are described below for the production method of composite powder with adhering zinc oxide.

Embodiment 4

A solution prepared by ultrasonic dispersion of iron oxide fine particles, which were used as seed particles, was added to a slurry of titanated mica. After the mixture is stirred, to this were simultaneously added a zinc chloride aqueous solution and an alkali aqueous solution that were prepared as described above. On this occasion, the mole ratio of the alkali ion and the zinc ion was set in a range of 1/2-2/1. The reaction temperature was set preferably at 0-90° C., more preferably at 10-60° C., and further more preferably at 20-40° C. It is preferable to always adjust the pH of the slurry in a range of 7-9 during the reaction.

Embodiment 5

200 ml of ion-exchanged water and 50 g of titanated mica, which acts as a substrate, were placed in a reaction vessel, and to this were installed a stirring device and a pH controller connected to two microtube pumps. The microtube pumps were connected to an aqueous solution containing 37.65 g of zinc chloride, which was dissolved in 150 ml of ion-exchanged water, and to an aqueous solution containing 25 g of sodium hydroxide, which was dissolved in 450 ml of ion-exchanged water, respectively. The microtube pumps were fixed so that the solutions can be added dropwise to the reaction vessel.

The reaction was conducted by adding the two aqueous solutions for approximately 20 minutes and with stirring at normal temperature and normal pressure. The drop volumes of the two aqueous solutions were adjusted during the reaction. The obtained product was filtered, washed with water, centrifuged three times each, dried in an oven at 80° C. for 15 hours, and then powdered with a mill. The obtained powder was screened with 100 mesh sieve to obtain a desired product.

The composite powder according to the present invention, explained so far, can be blended with any cosmetics without any limitation. However, from the standpoint of optical characteristics, it is preferable to use the composite powder for makeup cosmetics.

There is also no limitation for the amount of composite powder used for blending. However, for example, the effect to make skin surface unevenness look uniform can be obtained by blending the powder into skin care cosmetics such as an milky lotion. The correcting effect of skin surface unevenness is significant if a large amount of the composite powder is blended into makeup cosmetics such as a powder foundation as an extender pigment.

When a pigment with interference colors such as titanated mica is used as a substrate, in order to correct imperfections in skin color such as dullness, blotches, freckles, redness, and dark rings around the eyes, it is preferable to blend no less than 1 weight % of the composite powder with respect to cosmetics. If no less than 15 weight % of the composite powder is blended, whiteness is overemphasized and the finished makeup looks powdery. In addition, interference light is overemphasized, resulting in an undesirable unnatural finish. When the above-mentioned optical color correction and the new texture are considered, it is more preferable to blend no less than 3 weight % of the composite powder in order to render the makeup effect.

The composite powder according to the present invention may be used after surface treatment, to the extent that its effect is not jeopardized, with an agent that is usually used for the cosmetics pigments, such as silicone, acrylsilicone, metal soap, lecithin, amino acids, collagen, or fluorinated compounds.

Furthermore, to the cosmetics according to the present invention, one or more kind of other powder ingredients from the following may be blended if necessary. They are inorganic powders such as titanium oxide, zinc oxide, bengala, yellow iron oxide, black iron oxide, ultramarine, cerium oxide, talc, mica, sericite, kaolin, bentonite, clay, silicic acid, silicic acid anhydride, magnesium silicate, zinc stearate, fluorine-gold-mica, synthetic talc, barium sulfate, magnesium sulfate, calcium sulfate, boron nitride, bismuth oxychloride, alumina, zirconium dioxide, magnesium oxide, chromium oxide, calamine, magnesium carbonate, and composite powder thereof, and organic powders such as silicone powder, silicone elastic powder, polyurethane powder, cellulose powder, nylon powder, PMMA powder, starch, polyethylene powder and composite powder thereof.

Furthermore, to the cosmetics according to the present invention, one or more kind of other oil ingredients from the following may be blended if necessary. They are liquid paraffin, squalane, ester oils, diglycerides, triglycerides, perfluoropolyethers, vaseline, lanolin, ceresin, carnauba wax, solid paraffin, fatty acids, polyhydric alcohols, silicone resin, fluororesin, acrylic resin, vinyl pyrrolidone, etc.

Furthermore, to the cosmetics according to the present invention, pigment, pH conditioner, moisturizer, thickener, surfactant, dispersant, stabilizer, colorant, preservative, antioxidant, UV absorber, perfume, etc. may be suitably blended within a range that the purpose of the invention can be achieved.

The cosmetics according to the present invention are prepared in the normal method, and the examples of cosmetic types are emulsion foundation, powder foundation, oil foundation, eye shadow, cheek color, body powder, perfume powder, baby powder, face powder, emulsion, beauty lotion, face lotion, beauty cream, sunscreen lotion, etc.

In the following paragraphs, the present invention is explained in further detail with reference to examples. However, the present invention is not limited to these examples. The amount of each blended component in the example cosmetics is expressed in weight % with respect to the total weight of cosmetics.

Composite Powder with Adhering Barium Sulfate

Composite powders with adhering barium sulfate according to the present invention were prepared under various conditions (Examples 1-32).

Example 1

50 g of red interference titanated mica, used as a substrate, with a particle diameter of ca. 12 μm was weighed into a 1000 ml separable round bottom flask. To this was added 400 ml of ion-exchanged water, and the mixture was mixed with stirring. Separately, a 100 ml aqueous solution containing 4 g of alumina particles (8 weight % with respect to the titanated mica), which were used as seed particles, with a particle diameter of ca. 0.5 μm was prepared by ultrasonic dispersion, and the solution was added to the slurry of the above titanated mica. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were separately added to the slurry. As soon as the solutions were added, white barium sulfate was formed and deposited. The reaction was continued for 2 hours.

The reaction solution was cooled to room temperature, and the obtained solid product was allowed to precipitate, filtered, and washed. After the salt was removed, the product was dried at 120° C. for 12 hours. After the product was dried, it was powdered to obtain red interference white powder of Example 1. An SEM picture of its powder surface is shown in FIG. 1 (FIG. 1B is an enlarged image of FIG. 1A). The adherence rate of barium sulfate on the obtained powder was 45 weight % with respect to the titanated mica, which was a substrate.

Examples 2-4

50 g of various interference titanated mica (Example 2: yellow interference, Example 3: green interference, Example 4: blue interference) used as a substrate, with a particle diameter of ca. 12 μm was weighed into a 1000 ml separable round bottom flask. To this was added 400 ml of ion-exchanged water, and the mixture was mixed with stirring. Separately, a 100 ml aqueous solution containing alumina particles (1-12 weight % with respect to the titanated mica), which were used as seed particles, with a particle diameter of ca. 0.5 μm was prepared by ultrasonic dispersion, and the solution was added to the slurry of the above titanated mica. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were separately added to the slurry. As soon as the solutions were added, white barium sulfate was formed and deposited. The reaction was continued for 2 hours.

The reaction solution was cooled to room temperature, and the obtained solid product was allowed to precipitate, filtered, and washed. After the salt was removed, the product was dried at 120° C. for 12 hours. After the product was dried, it was powdered to obtain various interference white powders of Examples 2-4 (Example 2: yellow interference, Example 3: green interference, Example 4: blue interference). The adherence rate of barium sulfate on the obtained powders was 45 weight % with respect to the titanated mica, which was a substrate.

Examples 5-7

50 g of red interference titanated mica, used as a substrate, with a particle diameter of ca. 12 μm was weighed into a 1000 ml separable round bottom flask. To this was added 400 ml of ion-exchanged water, and the mixture was mixed with stirring. Separately, a 100 ml aqueous solution containing alumina particles (1-12 weight % with respect to the titanated mica), which were used as seed particles, with a particle diameter of ca. 0.5 μm was prepared by ultrasonic dispersion, and the solution was added to the slurry of the above titanated mica. The temperature of the titanated mica slurry was adjusted to 60° C., and 150 ml of barium chloride aqueous solution and 150 ml of sodium sulfate aqueous solution, which adjusted each concentrations to 15 weight % (Example 5), 30 weight % (Example 6), 100 weight % (Example 7) of the adherence rate of barium sulfate with respect to the titanated mica substrate, was added separately. As soon as the solutions were added, white barium sulfate was formed and deposited. The reaction was continued for 2 hours.

Figure 2:
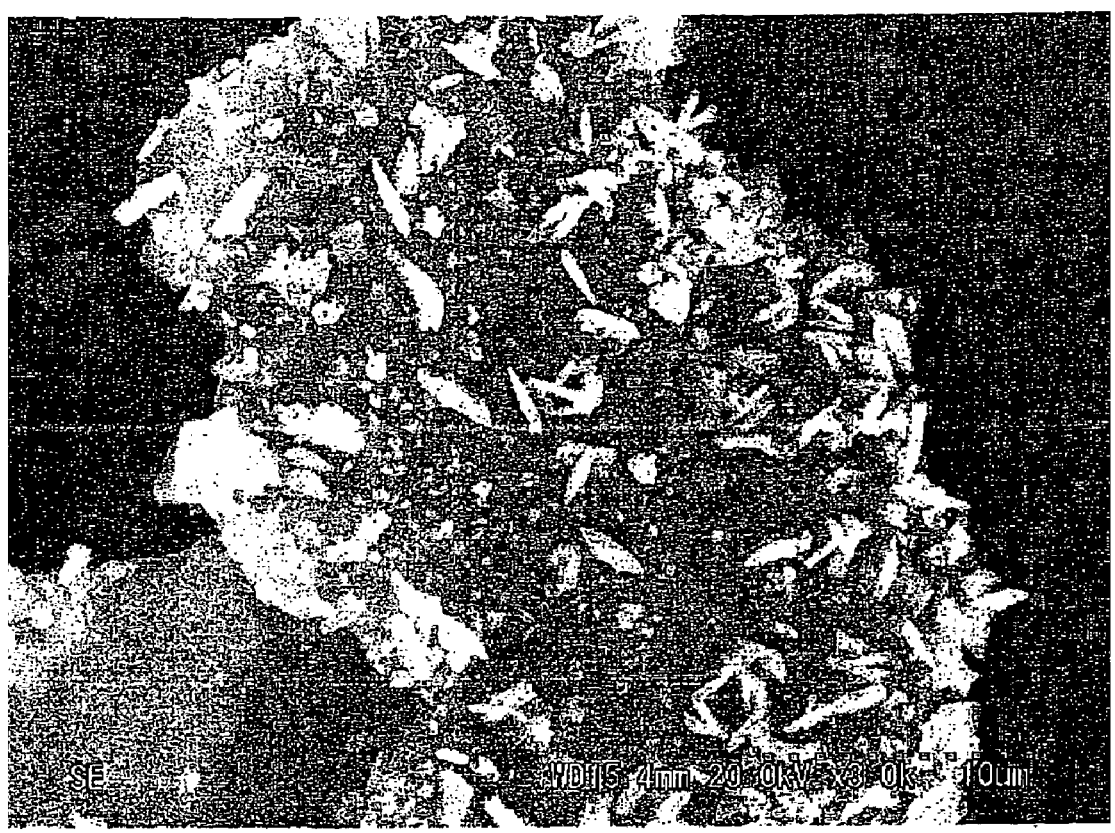
FIG. 2 shows an SEM picture of surface of a composite powder of Example 5.
Figure 3:
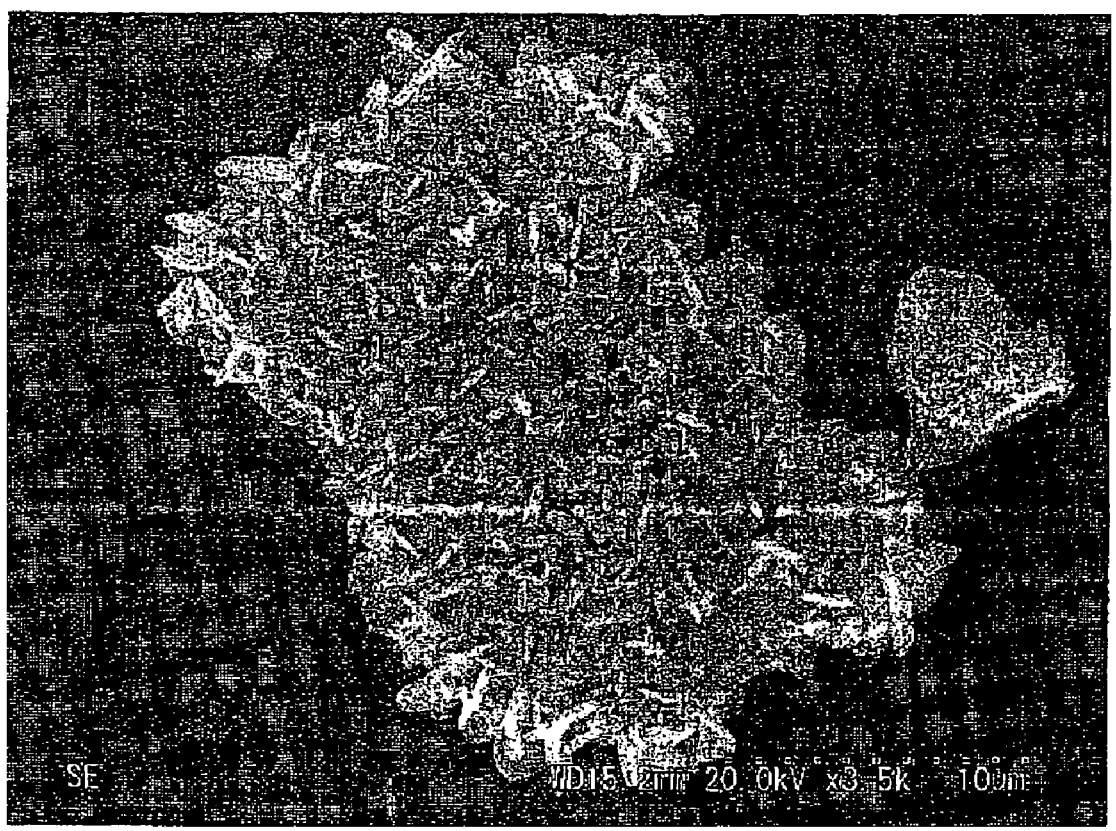
FIG. 3 shows an SEM picture of surface of a composite powder of Example 7.

The reaction solution was cooled to room temperature, and the obtained solid product was allowed to precipitate, filtered, and washed. After the salt was removed, the product was dried at 120° C. for 12 hours. After the product was dried, it was powdered to obtain red interference white powders of Examples 5-7. SEM pictures of its powder surfaces are shown in FIGS. 2 and 3 (Example 5 and 7).

Examples 8-10

50 g of red interference titanated mica, used as a substrate, with a particle diameter of ca. 12 μm was weighed into a 1000 ml separable round bottom flask. To this was added 400 ml of ion-exchanged water, and the mixture was mixed with stirring. Separately, a 100 ml aqueous solution containing alumina particles (1-12 weight % with respect to the titanated mica), which were used as seed particles, with a particle diameter of ca. 0.5 μm was prepared by ultrasonic dispersion, and the solution was added to the slurry of the above titanated mica. Furthermore, various metal chloride aqueous solution with a concentration of 964 mmol/L (Example 8: magnesium, Example 9: calcium, Example 10: sodium) was added for coexisting with metal ion. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were separately added to the slurry. As soon as the solutions were added, white barium sulfate was formed and deposited. The reaction was continued for 2 hours.

Figure 4:
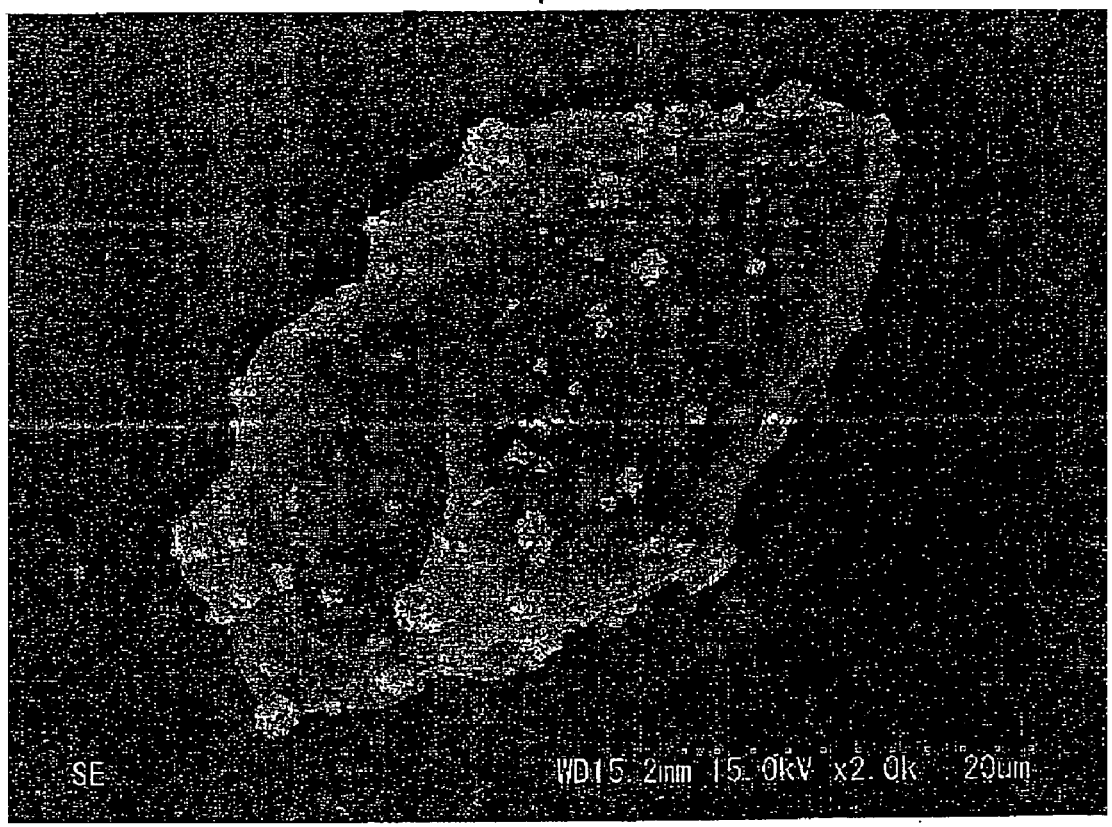
FIG. 4 shows an SEM picture of surface of a composite powder of Example 8.
Figure 5:
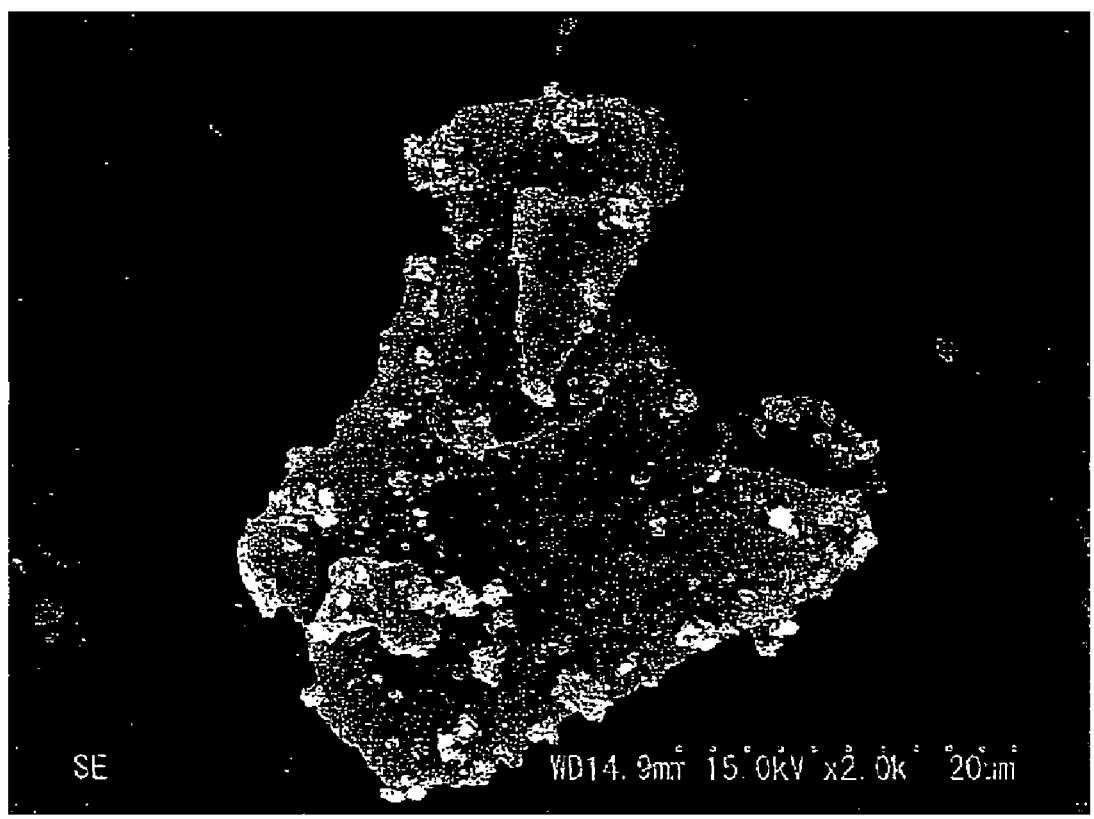
FIG. 5 shows an SEM picture of surface of a composite powder of Example 9.
Figure 6:
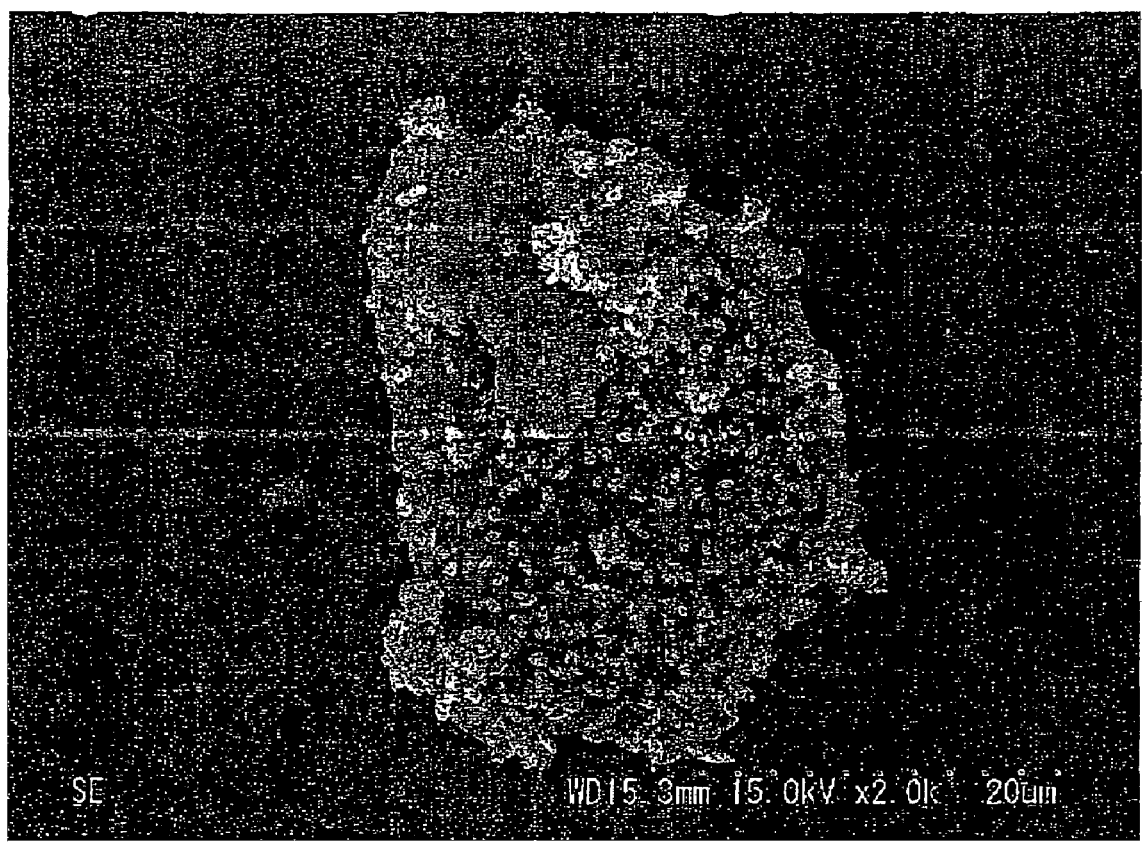
FIG. 6 shows an SEM picture of surface of a composite powder of Example 10.

The reaction solution was cooled to room temperature, and the obtained solid product was allowed to precipitate, filtered, and washed. After the salt was removed, the product was dried at 120° C. for 12 hours. After the product was dried, it was powdered to obtain red interference white powder of Examples 8-10. SEM pictures of its powder surfaces (Examples 8-10) are shown in FIG. 4-6. The adherence rate of barium sulfate on the obtained powder was 45 weight % with respect to the titanated mica, which was a substrate.

Examples 11-13

50 g of talc (Example 11), or mica (Example 12, 13), used as a substrate, with a particle diameter of ca. 12 μm was weighed into a 1000 ml separable round bottom flask. To this was added 400 ml of ion-exchanged water, and the mixture was mixed with stirring. Separately, a 100 ml aqueous solution containing alumina particles (1 weight % with respect to the talc or mica), which were used as seed particles, with a particle diameter of ca. 0.5 μm was prepared by ultrasonic dispersion, and the solution was added to the slurry of the above titanated mica. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were separately added to the slurry. As soon as the solutions were added, white barium sulfate was formed and deposited. The reaction was continued for 3 hours.

Figure 7:
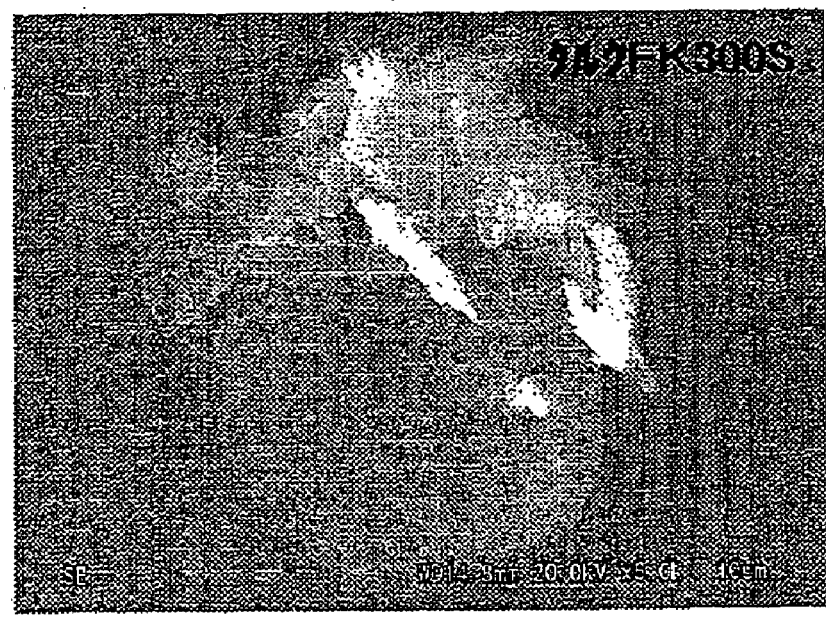
FIG. 7 shows an SEM picture of surface of a composite powder of Example 11.
Figure 8:
FIG. 8 shows an SEM picture of surface of a composite powder of Example 12.
Figure 9:
FIG. 9 shows an SEM picture of surface of a composite powder of Example 13.

The reaction solution was cooled to room temperature, and the obtained solid product was allowed to precipitate, filtered, and washed. After the salt was removed, the product was dried at 150° C. for 12 hours. After the product was dried, it was powdered to obtain white powder of Examples 11-13. SEM pictures of its powder surfaces (Examples 11-13) are shown in FIG. 7-9.

Example 14

50 g of red interference titanated mica, used as a substrate, with a particle diameter of ca. 12 μm was weighed into a 1000 ml separable round bottom flask. To this was added 400 g of 10 weight % of ethanol solution, and the mixture was mixed with stirring. Separately, a 100 ml aqueous solution containing alumina particles (1-12 weight % with respect to the titanated mica), which were used as seed particles, with a particle diameter of ca. 0.5 μm was prepared by ultrasonic dispersion, and the solution was added to the slurry of the above titanated mica. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were added to the slurry at the same time. As soon as the solutions were added, white barium sulfate was formed and deposited. The reaction was continued for 2 hours.

The reaction solution was cooled to room temperature, and the obtained solid product was allowed to precipitate, filtered, and washed. After the salt was removed, the product was dried at 120° C. for 12 hours. After the product was dried, it was powdered to obtain red interference white powder of Example 14. The adherence rate of barium sulfate on the obtained powder was 45 weight % with respect to the titanated mica, which was a substrate.

Example 15

50 g of red interference titanated mica, used as a substrate, with a particle diameter of ca. 12 μm was weighed into a 1000 ml separable round bottom flask. To this was added 400 ml of ion-exchanged water and 100 ml of aqueous solution dissolving 0.5 g of polyethyleneglycol (molecular weight of ca. 400), and the mixture was mixed with stirring. Separately, a 100 ml aqueous solution containing alumina particles (1-12 weight % with respect to the titanated mica), which were used as seed particles, with a particle diameter of ca. 0.5 μm was prepared by ultrasonic dispersion, and the solution was added to the slurry of the above titanated mica. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were added to the slurry at the same time. As soon as the solutions were added, white barium sulfate was formed and deposited. The reaction was continued for 2 hours.

The reaction solution was cooled to room temperature, and the obtained solid product was allowed to precipitate, filtered, and washed. After the salt was removed, the product was dried at 120° C. for 12 hours. After the product was dried, it was powdered to obtain red interference white powder of Example 15. The adherence rate of barium sulfate on the obtained powder was 45 weight % with respect to the titanated mica, which was a substrate.

Example 16

50 g of red interference titanated mica, used as a substrate, with a particle diameter of ca. 12 μm was weighed into a 1000 ml separable round bottom flask. To this was added 400 ml of ion-exchanged water, and the mixture was mixed with stirring. Separately, a 100 ml aqueous solution containing alumina particles (1-12 weight % with respect to the titanated mica), which were used as seed particles, with a particle diameter of ca. 0.5 μm was prepared by ultrasonic dispersion, and the solution was added to the slurry of the above titanated mica, and pH of the solution was adjusted to 8-9 by addition of hydrochloric acid dilute and/or sodium hydroxide dilute. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were added to the slurry at the same time while pH of the solution was adjusted to 8-9 by addition of hydrochloric acid dilute and/or sodium hydroxide dilute. As soon as the solutions were added, white barium sulfate was formed and deposited. The reaction was continued for 2 hours.

The reaction solution was cooled to room temperature, and the obtained solid product was allowed to precipitate, filtered, and washed. After the salt was removed, the product was dried at 120° C. for 12 hours. After the product was dried, it was powdered to obtain red interference white powder of Example 16. The adherence rate of barium sulfate on the obtained powder was 45 weight % with respect to the titanated mica, which was a substrate.

Examples 17-19

50 g of red interference titanated mica, used as a substrate, with a particle diameter of ca. 12 μm was weighed into a 1000 ml separable round bottom flask. To this was added 400 ml of ion-exchanged water, and the mixture was mixed with stirring. Separately, a 100 ml aqueous solution containing alumina particles (1-12 weight % with respect to the titanated mica), which were used as seed particles, with a particle diameter of ca. 0.5 μm was prepared by ultrasonic dispersion, and the solution was added to the slurry of the above titanated mica. Furthermore, various acid aqueous solutions with a concentration of 964 mmol/L (Example 17: acetic acid aqueous solution, Example 18: sodium L-glutamate aqueous solution, Example 19: sodium L-aspartate aqueous solution) were added. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were separately added to the slurry. As soon as the solutions were added, white barium sulfate was formed and deposited. The reaction was continued for 2 hours.

Figure 10:
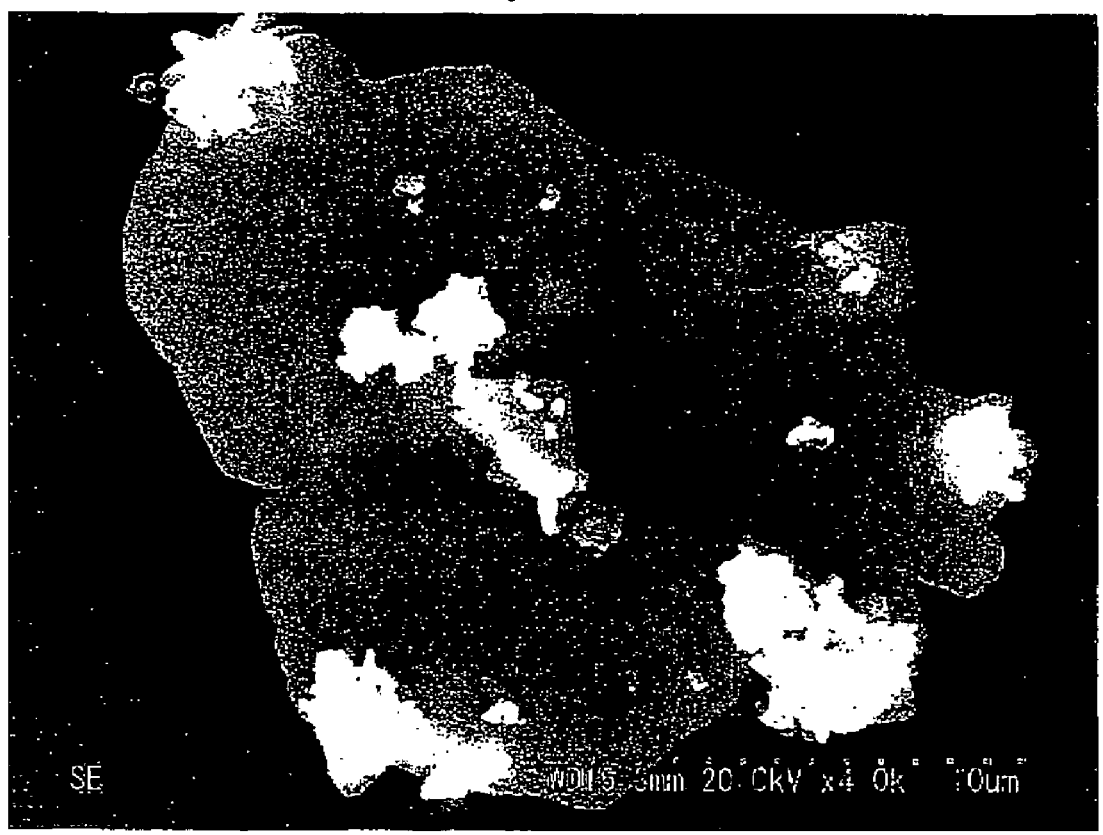
FIG. 10 shows an SEM picture of surface of a composite powder of Example 17.
Figure 12:
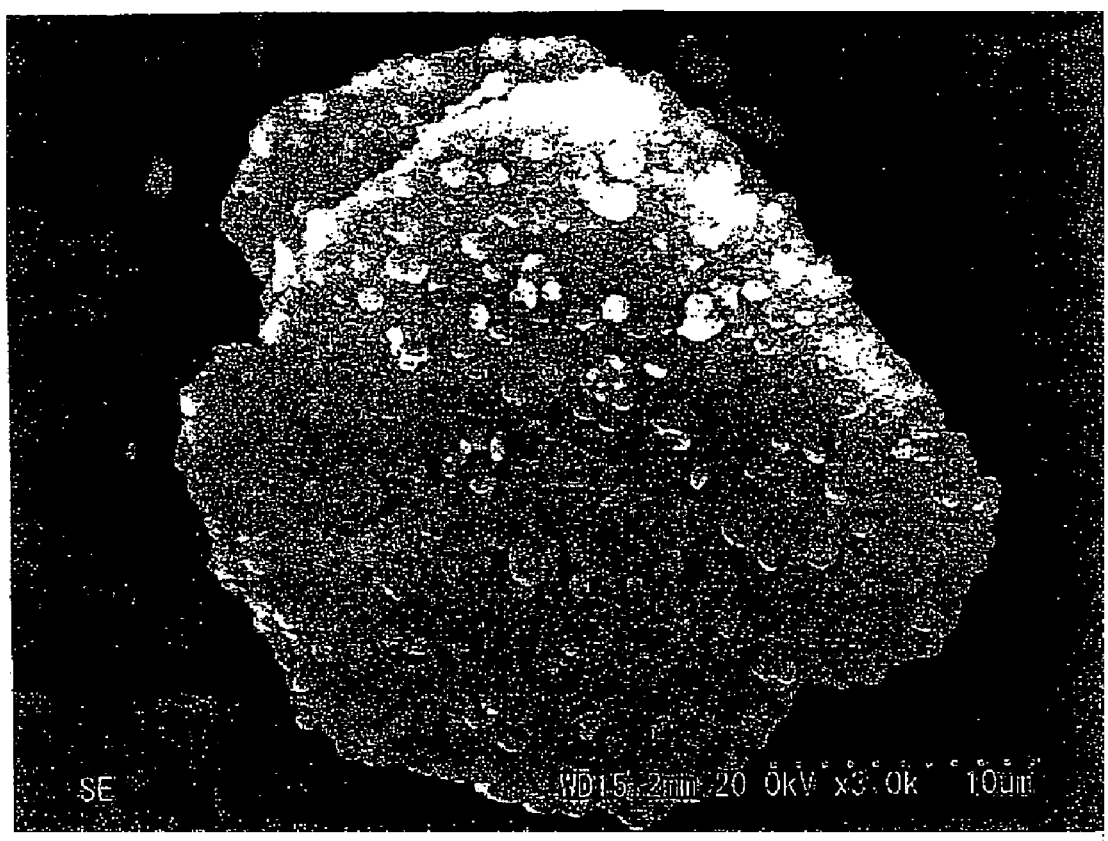
FIG. 12 shows an SEM picture of surface of a composite powder of Example 19.

The reaction solution was cooled to room temperature, and the obtained solid product was allowed to precipitate, filtered, and washed. After the salt was removed, the product was dried at 120° C. for 12 hours. After the product was dried, it was powdered to obtain red interference white powder of Examples 17-19. SEM pictures of its powder surfaces (Examples 17-19) are shown in FIG. 10-12. The adherence rate of barium sulfate on the obtained powder was 45 weight % with respect to the titanated mica, which was a substrate.

According to FIGS. 11 and 12, in Example 18 and 19, which were coexisted with sodium glutamate, sodium aspartate as complexing agent of barium ion, the barium sulfate particles adhered on substrate powder surface are spherical shape, and number average of the particle diameters are 0.8-3 μm.

Examples 20-22

50 g of red interference titanated mica, used as a substrate, with a particle diameter of ca. 12 μm was weighed into a 1000 ml separable round bottom flask. To this was added 400 ml of ion-exchanged water, and the mixture was mixed with stirring, and 3.6, 9, and 36 g of sodium L-glutamate as complexing agent (0.2, 0.5, and 2.0 equivalent with respect to barium ion, Example 20: 0.2 equivalent, Example 21: 0.5 equivalent, Example 22: 2.0 equivalent) were added. Separately, a 100 ml aqueous solution containing alumina particles (0.2-5 weight % with respect to the titanated mica), which were used as seed particles, with a particle diameter of ca. 0.03 μm was prepared by ultrasonic dispersion, and the solution was added to the slurry of the above titanated mica. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were separately added to the slurry. As soon as the solutions were added, white barium sulfate was formed and deposited. The reaction was continued for 1 hour.

Figure 14:
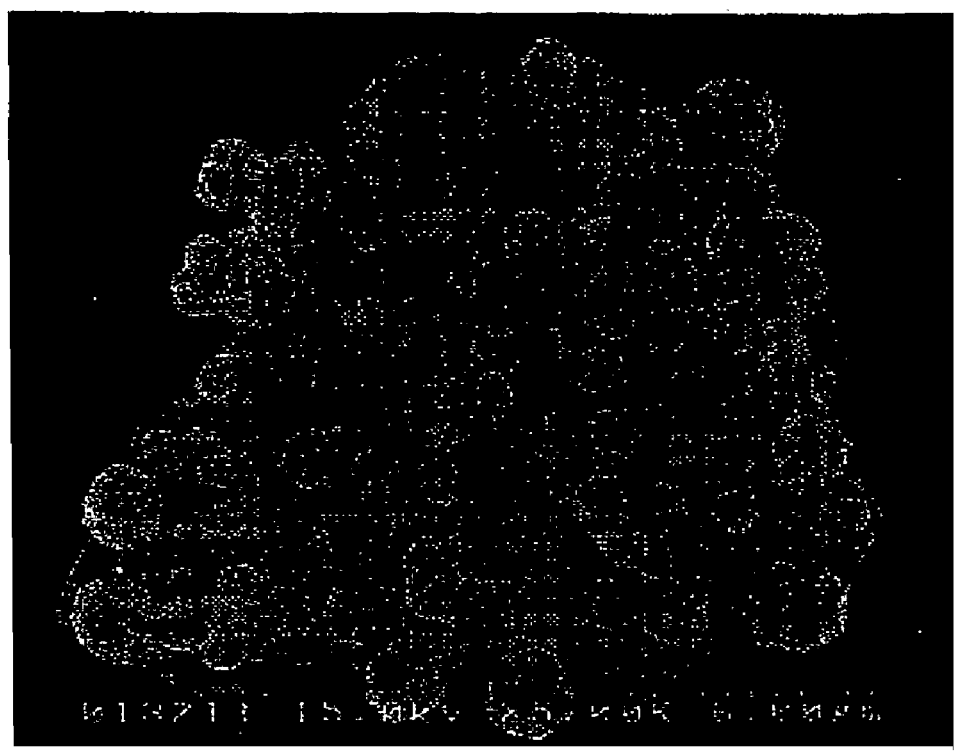
FIG. 14 shows an SEM picture of surface of a composite powder of Example 21.
Figure 15:
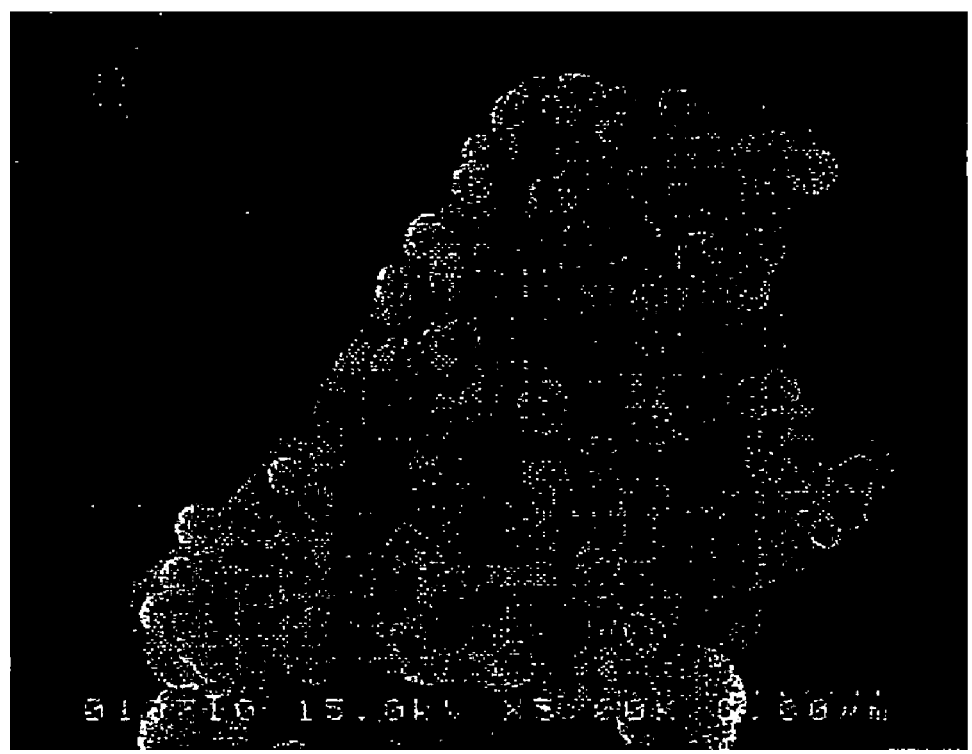
FIG. 15 shows an SEM picture of surface of a composite powder of Example 22.

The reaction solution was cooled to room temperature, and the obtained solid product was allowed to precipitate, filtered, and washed. After the salt was removed, the product was dried at 120° C. for 12 hours. After the product was dried, it was powdered to obtain red interference white powder of Examples 20-22. SEM pictures of its powder surface (Examples 20-22) are shown in FIG. 13-15.

Figure 13:
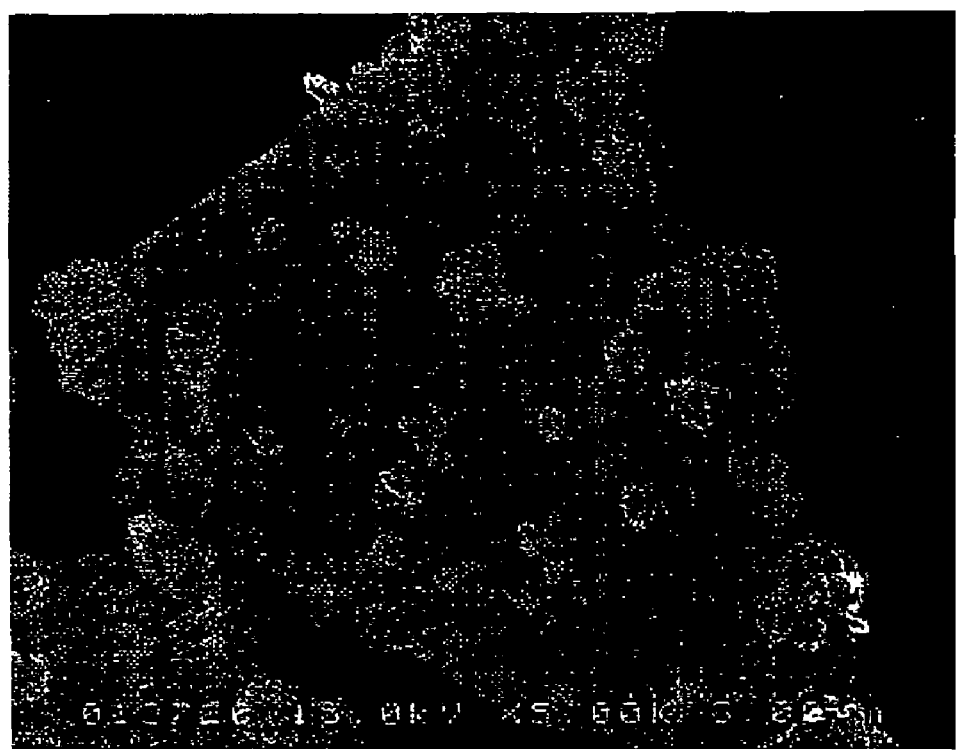
FIG. 13 shows an SEM picture of surface of a composite powder of Example 20.

According to FIG. 13, in Example 20, which was coexisted with 0.2 equivalent of sodium glutamate as complexing agent, the barium sulfate particles adhered on substrate powder surface are nearly polygon shape, and the particle diameter are small. On the other hand, in Example 21 which was coexisted with 0.5 equivalent of sodium glutamate, and in Example 22 which was coexisted with 2.0 equivalent of sodium glutamate, the barium sulfate particles are spherical shape, and number average of the particle diameters are 0.8-1.5 μm.

Examples 23-25

50 g of various interference titanated mica (Example 23: yellow interference, Example 24: green interference, Example 25: blue interference) used as a substrate, with a particle diameter of ca. 12 μm was weighed into a 1000 ml separable round bottom flask. To this was added 400 ml of ion-exchanged water, and the mixture was mixed with stirring, and 36 g of sodium L-glutamate as complexing agent (2.0 equivalent with respect to barium ion) was added. Separately, a 100 ml aqueous solution containing alumina particles (0.2-5 weight % with respect to the titanated mica), which were used as seed particles, with a particle diameter of ca. 0.03 μm was prepared by ultrasonic dispersion, and the solution was added to the slurry of the above titanated mica. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were separately added to the slurry. As soon as the solutions were added, white barium sulfate was formed and deposited. The reaction was continued for 1 hour.

The reaction solution was cooled to room temperature, and the obtained solid product was allowed to precipitate, filtered, and washed. After the salt was removed, the product was dried at 120° C. for 12 hours. After the product was dried, it was powdered to obtain various interference white powders of Examples 23-25 (Example 23: yellow interference, Example 24: green interference, Example 25: blue interference). The adherence rate of barium sulfate on the obtained powder was 45 weight % with respect to the titanated mica, which was a substrate, the barium sulfate particles adhered on substrate powder surface are spherical shape, and number average of the particle diameters are 0.5-3 μm.

Examples 26-29

50 g of various extending pigment (Example 26: mica, Example 27: synthetic mica, Example 28: plate-shaped talc Example 29: sericite) used as a substrate, with a particle diameter of ca. 12 μm were weighed into a 1000 ml separable round bottom flask. To this was added 400 ml of ion-exchanged water, and the mixture was mixed with stirring, and 36 g of sodium L-glutamate as complexing agent (2.0 equivalent with respect to barium ion) was added. Separately, a 100 ml aqueous solution containing alumina particles (1 weight % with respect to the talc or mica), which were used as seed particles, with a particle diameter of ca. 0.5 μm was prepared by ultrasonic dispersion, and the solution was added to the slurry of the above titanated mica. The temperature of the titanated mica slurry was adjusted to 60° C., and 150 ml of barium chloride aqueous solution with a concentration of 850 mmol/L and 150 ml of sodium sulfate aqueous solution with a concentration of 850 mmol/L were separately added to the slurry. As soon as the solutions were added, white barium sulfate was formed and deposited. The reaction was continued for 3 hours.

The reaction solution was cooled to room temperature, and the obtained solid product was allowed to precipitate, filtered, and washed. After the salt was removed, the product was dried at 120° C. for 12 hours. After the product was dried, it was powdered to obtain various interference white powders of Examples 26-29 (Example 26: mica, Example 27: synthetic mica, Example 28: plate-shaped talc Example 29: sericite). The adherence rate of barium sulfate on the obtained powder was 60 weight % with respect to the titanated mica, which was a substrate, the barium sulfate particles adhered on substrate powder surface are spherical shape, and number average of the particle diameters are 1-3 μm.

Examples 30-32

50 g of red interference titanated mica, used as a substrate, with a particle diameter of ca. 12 μm was weighed into a 1000 ml separable round bottom flask. To this was added 400 ml of ion-exchanged water, and the mixture was mixed with stirring, and various complexing agents (Example 30: succinic acid, Example 31: sodium citrate, Example 32: EDTA), which were an amount of 2.0 equivalent with respect to barium ion, were added. Separately, a 100 ml aqueous solution containing alumina particles (0.2-5 weight % with respect to the titanated mica), which were used as seed particles, with a particle diameter of ca. 0.03 μm was prepared by ultrasonic dispersion, and the solution was added to the slurry of the above titanated mica. The temperature of the titanated mica slurry was adjusted to 60° C., and 150 ml of barium chloride aqueous solution with a concentration of 640 mmol/L and 150 ml of sodium sulfate aqueous solution with a concentration of 640 mmol/L were separately added to the slurry. As soon as the solutions were added, white barium sulfate was formed and deposited. The reaction was continued for 2 hours.

The reaction solution was cooled to room temperature, and the obtained solid product was allowed to precipitate, filtered, and washed. After the salt was removed, the product was dried at 120° C. for 12 hours. After the product was dried, it was powdered to obtain various interference white powders of Examples 30-32. The adherence rate of barium sulfate on the obtained powder was 45 weight % with respect to the titanated mica, which was a substrate, the barium sulfate particles adhered on substrate powder surface are spherical shape, and number average of the particle diameters are 0.5-4 μm.

Comparative Example 1

A powder covered with barium sulfate was obtained by a similar preparation method to that of Example 1, except for the addition of no seed particles, and for the adjustment of suitable amount of ion-exchanged water.

Comparative Example 2

A powder covered with barium sulfate was obtained by a similar preparation method to that of example 1 except for the addition of no seed particles, for the addition of 36 g sodium L-glutamate (2 equivalents to barium ion) as a complexing agent, and for the adjustment of suitable amount of ion-exchanged water.

Comparative Example 3

Barium sulfate powder was obtained by a similar preparation method to that of example 1 except for the addition of no substrate powder particles, and for the adjustment of suitable amount of ion-exchanged water. The barium sulfate particles were spherical, and the average particle diameter was ca. 2 µm.

Various cosmetics containing composite powders of the above examples were evaluated. The cosmetics were applied to 20 female panel members, and the application characteristics such as effectiveness in correcting skin surface unevenness (pores, fine wrinkles, etc. of the skin) and imperfections in skin color (dullness, blotches, freckles, redness, dark rings around the eyes, etc.), clearness, natural finish, and feeling of touch at the time of application (smoothness) were evaluated based on the criteria described below.

Evaluation Criteria for Application Characteristics
◎ More than 16 persons answered "good".
○ 12-16 persons answered "good".
Δ 9-11 persons answered "good".
X 5-8 persons answered "good".
XX Less than 5 persons answered "good".

Formulations of cosmetics and their evaluation results are shown below.

TABLE 1

Powder foundation

|  | Example 33 | Comparative Example 4 | Comparative Example 5 |
|---|---|---|---|
| Sericite | 17 | 17 | 17 |
| Synthetic mica | 10 | 10 | 10 |
| Talc | Balance | Balance | Balance |
| Red interference composite powder (Example 1) | 8 | — | — |
| Composite powder (Comparative Example 1) | — | 8 | — |
| Red interference titanated mica | — | — | 8 |
| Titanium oxide | 10 | 10 | 10 |
| Bengala | 0.8 | 0.8 | 0.8 |
| Yellow iron oxide | 2 | 2 | 2 |
| Black iron oxide | 0.1 | 0.1 | 0.1 |
| Zinc oxide | 2 | 2 | 2 |
| Silicone elastic powder | 2 | 2 | 2 |
| Dimethylpolysiloxane | 3 | 3 | 3 |
| Liquid paraffin | 5 | 5 | 5 |
| Petrolatum | 5 | 5 | 5 |
| Sorbitan sesquiisostearate | 1 | 1 | 1 |
| Paraben | q.s | q.s | q.s |
| Antioxidant | q.s | q.s | q.s |
| Perfume | q.s | q.s | q.s |
| Correction effect for skin unevenness | ○ | X | XX |
| Correction effect for skin dullness | ◎ | Δ | ○ |
| Clearness of finished makeup | ◎ | Δ | Δ |
| Naturality of finished makeup | ○ | Δ | X |
| Feeling of touch (smoothness) | ◎ | ○ | Δ |

As is clear from Table 1, the foundation of Example 33 containing the composite powder of Example 1 was effective in correcting skin surface unevenness and imperfections in skin color, and it was also effective in rendering a natural finish with clearness. In addition, the feeling of touch upon application was smooth and light.

On the other hand, the foundation of Comparative Example 4 containing the composite powder of Comparative Example 1 was not effective in correcting skin surface unevenness and imperfections in skin color, and it was also not effective in rendering a natural finish with clearness. The foundation of Comparative Example 5 containing interference titanated mica could correct imperfections in skin color. However, skin surface unevenness was conspicuous, there was a glare, and a natural finish with clearness could not be achieved.

TABLE 2

Powder foundation (summer powder cake-type foundation allowing water use)

|  | Example 34 | Comparative Example 6 | Comparative Example 7 |
|---|---|---|---|
| Siliconized sericite | 18 | 18 | 18 |
| Siliconized mica | Balance | Balance | Balance |
| Siliconized talc | 15 | 15 | 15 |
| Siliconized yellow interference composite powder (Example 2) | 8 | — | — |
| Siliconized composite powder (Comparative Example 1) | — | 8 | — |
| Siliconized yellow interference titanated mica | — | — | 8 |
| Siliconized titanium oxide | 8 | 8 | 8 |
| Aluminum stearate treated fine particle titanium oxide | 6 | 6 | 6 |
| Siliconized bengala | 1.2 | 1.2 | 1.2 |
| Siliconized yellow iron oxide | 2.5 | 2.5 | 2.5 |
| Siliconized black iron oxide | 0.9 | 0.9 | 0.9 |
| Polyurethane powder | 2 | 2 | 2 |
| Paraben | q.s | q.s | q.s |
| Dimethylpolysiloxane | 4 | 4 | 4 |
| Methylphenylpolysiloxane | 3 | 3 | 3 |
| Octyl methoxycinnamate | 3 | 3 | 3 |
| Polyether modified silicone | 2 | 2 | 2 |
| Antioxidant | q.s | q.s | q.s |
| Perfume | q.s | q.s | q.s |
| Correction effect for skin unevenness | ○ | X | XX |
| Correction effect for blotches and freckles | ◎ | Δ | Δ |
| Clearness of finished makeup | ◎ | Δ | X |
| Naturality of finished makeup | ○ | Δ | X |
| Feeling of touch (smoothness) | ◎ | ○ | Δ |

As is clear from Table 2, the foundation of Example 34 containing the composite powder of Example 2 was effective in correcting skin surface unevenness and imperfections in skin color, and it was also effective in rendering a natural finish with clearness. In addition, the feeling of touch upon application was smooth and light.

On the other hand, the foundation of Comparative Example 6 containing the powder of Comparative Example 1 was not effective in correcting skin surface unevenness, and it was also not effective enough in rendering a natural finish with clearness. With the foundation of Comparative Example 7 containing interference titanated mica, skin surface unevenness was conspicuous, there was a glare, and a natural finish with clearness could not be achieved.

TABLE 3

Powder foundation (summer powder cake-type foundation allowing water use)

|  | Example 35 | Comparative Example 8 | Comparative Example 9 |
|---|---|---|---|
| Siliconized mica | 25 | 25 | 25 |
| Siliconized sericite | 17 | 17 | 17 |
| Siliconized talc | Balance | Balance | Balance |
| Siliconized blue interference composite powder (Example 4) | 8 | — | — |
| Siliconized composite powder (Comparative Example 1) | — | 8 | — |
| Siliconized blue interference titanated mica | — | — | 8 |

TABLE 3-continued

Powder foundation (summer powder cake-type foundation allowing water use)

| | Example 35 | Comparative Example 8 | Comparative Example 9 |
|---|---|---|---|
| Siliconized titanium oxide | 10 | 10 | 10 |
| Spherical PMMA powder | 4 | 4 | 4 |
| Paraben | q.s | q.s | q.s |
| Dimethylpolysiloxane | 4 | 4 | 4 |
| Methylphenylpolysiloxane | 1 | 1 | 1 |
| Petrolatum | 3 | 3 | 3 |
| Octyl methoxycinnamate | 3 | 3 | 3 |
| Sorbitan diisostearate | 1 | 1 | 1 |
| Antioxidant | q.s | q.s | q.s |
| Perfume | q.s | q.s | q.s |
| Correction effect for skin unevenness | ○ | X | X |
| Correction effect for skin color | ○ | Δ | Δ |
| Clearness of finished makeup | ⊚ | Δ | X |
| Naturality of finished makeup | ⊚ | Δ | X |
| Feeling of touch (smoothness) | ○ | ○ | Δ |

As is clear from Table 3, the foundation of Example 35 containing the composite powder of Example 4 was effective in correcting skin surface unevenness and imperfections in skin color, and it was also effective in rendering a natural finish with clearness. In addition, the feeling of touch upon application was smooth and light.

On the other hand, the foundation of Comparative Example 8 containing the powder of Comparative Example 1 was not effective in correcting skin surface unevenness, and it was also not effective enough in rendering a natural finish with clearness. With the foundation of Comparative Example 9 containing interference titanated mica, skin surface unevenness was conspicuous, there was a glare, and a natural finish with clearness could not be achieved.

TABLE 4

Face powder

| | Example 36 | Example 37 | Example 38 |
|---|---|---|---|
| Talc | Balance | Balance | Balance |
| Mica | 20 | 20 | 20 |
| Plate-shaped barium sulfate | 5 | 5 | 5 |
| Red interference composite powder (Example 1) | 10 | — | — |
| Red interference composite powder (Example 5) | — | 10 | — |
| Red interference composite powder (Example 7) | — | — | 10 |
| Fine particle titanated mica | 3 | 3 | 3 |
| Spherical silicone powder | 3 | 3 | 3 |
| Petrolatum | 1 | 1 | 1 |
| Squalane | 3 | 3 | 3 |
| Ester oil | 1 | 1 | 1 |
| Paraben | q.s | q.s | q.s |
| Antioxidant | q.s | q.s | q.s |
| Perfume | q.s | q.s | q.s |
| Correction effect for skin unevenness | ○ | Δ | ⊚ |
| Correction effect for skin dullness | ⊚ | ⊚ | Δ |
| Clearness of finished makeup | ⊚ | ○ | Δ |
| Naturality of finished makeup | ○ | Δ | ○ |
| Feeling of touch (smoothness) | ⊚ | Δ | ⊚ |

As is clear from Table 4, the face powders of Examples 36, 37, and 38 containing the composite powders of Examples 1, 5, and 7, respectively, were effective in correcting skin surface unevenness and imperfections in skin color, and they were also effective in rendering a natural finish with clearness. In addition, the feeling of touch upon application was smooth and light.

TABLE 5

W/O type emulsified cream foundation

| | Example 39 | Comparative Example 10 | Comparative Example 11 |
|---|---|---|---|
| Ion-exchange water | 43 | 43 | 43 |
| Sodium chondroitin sulfate | 1 | 1 | 1 |
| 1,3-butylene glycol | 3 | 3 | 3 |
| Methylparaben | q.s | q.s | q.s |
| Dimethylpolysiloxane (20 cs) | 16 | 16 | 16 |
| Decamethylcyclopentasiloxane | 5 | 5 | 5 |
| Silicone resin | 1 | 1 | 1 |
| Cetyl isooctanate | 1 | 1 | 1 |
| Polyoxyalkylene modified organopolysiloxane (modification rate 20%) | 4 | 4 | 4 |
| Antioxidant | q.s | q.s | q.s |
| Perfume | q.s | q.s | q.s |
| Spherical silica | 5 | 5 | 5 |
| Siliconized titanium oxide | 10 | 10 | 10 |
| Siliconized red interference composite powder (Example 15) | 6 | — | — |
| Siliconized composite powder (Comparative Example 1) | — | 6 | — |
| Siliconized red interference titanated mica | — | — | 6 |
| Siliconized bengala | 1.4 | 1.4 | 1.4 |
| Siliconized yellow iron oxide | 3 | 3 | 3 |
| Siliconized black iron oxide | 0.1 | 0.1 | 0.1 |
| Correction effect for skin unevenness | ⊚ | Δ | Δ |
| Correction effect for skin dullness | ○ | Δ | Δ |
| Clearness of finished makeup | ○ | ○ | ○ |
| Naturality of finished makeup | ○ | ○ | Δ |
| Feeling of touch (smoothness) | ⊚ | Δ | ⊚ |

As is clear from Table 5, the foundation of Example 39 containing the composite powder of Example 15 was effective in correcting skin surface unevenness and imperfections in skin color, and it was also effective in rendering a natural finish with clearness. In addition, the feeling of touch upon application was smooth and light.

On the other hand, the foundation of Comparative Example 10 containing the composite powder of Comparative Example 1 was not effective in correcting skin surface unevenness and imperfections in skin color, and it was also not effective in rendering a natural finish with clearness. The foundation of Comparative Example 11 containing interference titanated mica could correct imperfections in skin color. However, skin surface unevenness was conspicuous, there was a glare, and a natural finish with clearness could not be achieved.

TABLE 6

W/O type emulsified cream foundation (cake-type)

| | Example 40 | Comparative Example 12 | Comparative Example 13 |
|---|---|---|---|
| Ion-exchange water | 40.5 | 40.5 | 40.5 |
| Sodium glutamate | 1 | 1 | 1 |
| 1,3-butylene glycol | 5 | 5 | 5 |
| Methylparaben | q.s | q.s | q.s |
| Dimethylpolysiloxane (20 cs) | 4 | 4 | 4 |
| Decamethylcyclopentasiloxane | 16 | 16 | 16 |
| Silicone resin | 1 | 1 | 1 |

TABLE 6-continued

W/O type emulsified cream foundation (cake-type)

| | Example 40 | Comparative Example 12 | Comparative Example 13 |
|---|---|---|---|
| Cetyl isooctanate | 1 | 1 | 1 |
| Polyoxyalkylene modified organopolysiloxane (modification rate 20%) | 4 | 4 | 4 |
| Antioxidant | q.s | q.s | q.s |
| Perfume | q.s | q.s | q.s |
| Wax | 5 | 5 | 5 |
| Siliconized titanium oxide | 8 | 8 | 8 |
| Siliconized bengala | 0.5 | 0.5 | 0.5 |
| Siliconized fine particle titanium oxide | 6 | 6 | 6 |
| Siliconized red interference composite powder (Example 16) | 6 | — | — |
| Siliconized composite powder (Comparative Example 1) | — | 6 | — |
| Siliconized red interference titanated mica | — | — | 6 |
| Siliconized black iron oxide | 0.1 | 0.1 | 0.1 |
| Siliconized yellow iron oxide | 1.4 | 1.4 | 1.4 |
| Correction effect for skin unevenness | ◎ | Δ | Δ |
| Correction effect for skin dullness | ◎ | Δ | ○ |
| Clearness of finished makeup | ○ | ○ | Δ |
| Naturality of finished makeup | ○ | ○ | Δ |
| Feeling of touch (smoothness) | ◎ | Δ | ◎ |

As is clear from Table 6, the foundation of Example 40 containing the composite powder of Example 16 was effective in correcting skin surface unevenness and imperfections in skin color, and it was also effective in rendering a natural finish with clearness. In addition, the feeling of touch upon application was smooth and light.

On the other hand, the foundation of Comparative Example 12 containing the composite powder of Comparative Example 1 was not effective in correcting skin surface unevenness and imperfections in skin color, and it was also not effective in rendering a natural finish with clearness. The foundation of Comparative Example 13 containing interference titanated mica could correct imperfections in skin color. However, skin surface unevenness was conspicuous, there was a glare, and a natural finish with clearness could not be achieved.

TABLE 7

Powder foundation

| | Example 41 | Comparative Example 14 | Comparative Example 15 |
|---|---|---|---|
| Sericite | 17 | 17 | 17 |
| Synthetic mica | 10 | 10 | 10 |
| Talc | Balance | Balance | Balance |
| Red interference composite powder (Example 18) | 8 | — | — |
| Composite powder (Comparative Example 1) | — | 8 | — |
| Red interference titanated mica | — | — | 8 |
| Titanium oxide | 10 | 10 | 10 |
| Bengala | 0.8 | 0.8 | 0.8 |
| Yellow iron oxide | 2 | 2 | 2 |
| Black iron oxide | 0.1 | 0.1 | 0.1 |
| Zinc oxide | 2 | 2 | 2 |
| Silicone elastic powder | 2 | 2 | 2 |
| Dimethylpolysiloxane | 3 | 3 | 3 |
| Liquid paraffin | 5 | 5 | 5 |
| Petrolatum | 5 | 5 | 5 |
| Sorbitan sesquiisostearate | 1 | 1 | 1 |
| Paraben | q.s | q.s | q.s |
| Antioxidant | q.s | q.s | q.s |
| Perfume | q.s | q.s | q.s |
| Correction effect for skin unevenness | ○ | X | XX |
| Correction effect for skin dullness | ◎ | Δ | ○ |
| Clearness of finished makeup | ◎ | Δ | Δ |
| Naturality of finished makeup | ○ | Δ | X |
| Feeling of touch (smoothness) | ◎ | ○ | Δ |

As is clear from Table 7, the foundation of Example 41 containing the composite powder of Example 18 was effective in correcting skin surface unevenness and imperfections in skin color, and it was also effective in rendering a natural finish with clearness. In addition, the feeling of touch upon application was smooth and light.

On the other hand, the foundation of Comparative Example 14 containing the composite powder of Comparative Example 1 was not effective in correcting skin surface unevenness and imperfections in skin color, and it was also not effective in rendering a natural finish with clearness. The foundation of Comparative Example 15 containing interference titanated mica could correct imperfections in skin color. However, skin surface unevenness was conspicuous, there was a glare, and a natural finish with clearness could not be achieved.

TABLE 8

Powder foundation (summer powder cake-type foundation allowing water use)

| | Example 42 | Comparative Example 16 | Comparative Example 17 |
|---|---|---|---|
| Siliconized sericite | 18 | 18 | 18 |
| Siliconized mica | Balance | Balance | Balance |
| Siliconized talc | 15 | 15 | 15 |
| Siliconized yellow interference composite powder (Example 23) | 8 | — | — |
| Siliconized composite powder (Comparative Example 1) | — | 8 | — |
| Siliconized yellow interference titanated mica | — | — | 8 |
| Siliconized titanium oxide | 8 | 8 | 8 |
| Aluminum stearate treated fine particle titanium oxide | 6 | 6 | 6 |
| Siliconized bengala | 1.2 | 1.2 | 1.2 |
| Siliconized yellow iron oxide | 2.5 | 2.5 | 2.5 |
| Siliconized black iron oxide | 0.9 | 0.9 | 0.9 |
| Polyurethane powder | 2 | 2 | 2 |
| Paraben | q.s | q.s | q.s |
| Dimethylpolysiloxane | 4 | 4 | 4 |
| Methylphenylpolysiloxane | 3 | 3 | 3 |
| Octyl methoxycinnamate | 3 | 3 | 3 |
| Polyether modified silicone | 2 | 2 | 2 |
| Antioxidant | q.s | q.s | q.s |
| Perfume | q.s | q.s | q.s |
| Correction effect for skin unevenness | ○ | X | XX |
| Correction effect for skin blotches and freckles | ◎ | Δ | Δ |
| Clearness of finished makeup | ◎ | Δ | X |
| Naturality of finished makeup | ○ | Δ | X |
| Feeling of touch (smoothness) | ◎ | ○ | Δ |

As is clear from Table 8, the foundation of Example 42 containing the composite powder of Example 23 was effective in correcting skin surface unevenness and imperfections in skin color, and it was also effective in rendering a natural finish with clearness. In addition, the feeling of touch upon application was smooth and light.

On the other hand, the foundation of Comparative Example 16 containing the powder of Comparative Example 1 was not effective in correcting skin surface unevenness, and it was also not effective enough in rendering a natural finish with clearness. With the foundation of Comparative Example 17 containing interference titanated mica, skin surface unevenness was conspicuous, there was a glare, and a natural finish with clearness could not be achieved.

TABLE 9

Powder foundation (summer powder cake-type foundation allowing water use)

| | Example 43 | Comparative Example 18 | Comparative Example 19 |
|---|---|---|---|
| Siliconized mica | 8 | 8 | 18 |
| Siliconized sericite | 17 | 17 | 17 |
| Siliconized talc | Balance | Balance | Balance |
| Siliconized red interference composite powder (Example 18) | 25 | — | — |
| Siliconized composite powder (Comparative Example 2) | — | 25 | — |
| Siliconized composite powder (Comparative Example 3) | — | — | 15 |
| Siliconized titanium oxide | 10 | 10 | 10 |
| Spherical PMMA powder | 4 | 4 | 4 |
| Paraben | q.s | q.s | q.s |
| Dimethylpolysiloxane | 4 | 4 | 4 |
| Methylphenylpolysiloxane | 1 | 1 | 1 |
| Petrolatum | 3 | 3 | 3 |
| Octyl methoxycinnamate | 3 | 3 | 3 |
| Sorbitan diisostearate | 1 | 1 | 1 |
| Antioxidant | q.s | q.s | q.s |
| Perfume | q.s | q.s | q.s |
| Correction effect for skin unevenness | ○ | X | Δ |
| Correction effect for skin color | ○ | X | Δ |
| Clearness of finished makeup | ◎ | Δ | Δ |
| Naturality of finished makeup | ◎ | Δ | ○ |
| Feeling of touch (smoothness) | ○ | Δ | Δ |

As is clear from Table 9, the foundation of Example 43 containing the composite powder of Example 18 was effective in correcting skin surface unevenness and imperfections in skin color, and it was also effective in rendering a natural finish with clearness. In addition, the feeling of touch upon application was smooth and light.

On the other hand, the foundation of Comparative Example 18 containing the composite powder of Comparative Example 2 was not effective in correcting skin surface unevenness, and it was also not effective enough in rendering a natural finish with clearness. With the foundation of Comparative Example 19 containing spherical barium sulfate powder of Comparative Example 3, skin surface unevenness was conspicuous, there was a glare, and a natural finish with clearness could not be achieved.

TABLE 10

Face powder

| | Example 44 | Example 45 | Example 46 |
|---|---|---|---|
| Talc | Balance | Balance | Balance |
| Mica | 20 | 20 | 20 |
| Plate-shaped barium sulfate | 5 | 5 | 5 |
| Red interference composite powder (Example 18) | 10 | — | — |
| Synthetic mica composite powder (Example 27) | — | 10 | — |
| Sericite composite powder (Example 29) | — | — | 10 |
| Fine particle titanium oxide | 3 | 3 | 3 |
| Spherical silicone powder | 3 | 3 | 3 |
| Petrolatum | 1 | 1 | 1 |
| Squalane | 3 | 3 | 3 |
| Ester oil | 1 | 1 | 1 |
| Paraben | q.s | q.s | q.s |
| Antioxidant | q.s | q.s | q.s |
| Perfume | q.s | q.s | q.s |
| Correction effect for skin unevenness | ○ | Δ | ◎ |
| Correction effect for skin dullness | ◎ | ◎ | Δ |
| Clearness of finished makeup | ◎ | ○ | Δ |
| Naturality of finished makeup | ○ | Δ | ○ |
| Feeling of touch (smoothness) | ○ | Δ | ◎ |

As is clear from Table 10, the face powders of Examples 44, 45, and 46 containing the composite powders of Examples 18, 27, and 29, respectively, were effective in correcting skin surface unevenness and imperfections in skin color, and they were also effective in rendering a natural finish with clearness. In addition, the feeling of touch upon application was smooth and light.

Formulations of other examples are shown below.

TABLE 11

O/W type emulsified cream foundation

| | Example 47 |
|---|---|
| Talc | 8 |
| Sericite | 7 |
| Red interference composite powder (Example1) | 6 |
| Titanium oxide | 10 |
| Bengala | 0.3 |
| Yellow iron oxide | 1.2 |
| Black iron oxide | 0.6 |
| Spherical polyethylene powder | 6 |
| Squalane | 10 |
| Olive oil | 10 |
| Stearic acid | 2 |
| Glyceryl monostearate | 2 |
| Sorbitan POE(40) monostearate | 2 |
| Glycerin | 5 |
| Triethanolamine | 0.8 |
| pH adjuster | q.s |
| Preservative | q.s |
| Ion-exchange water | Balance |

TABLE 12

Loose powder (powder foundation)

| | Example 48 |
|---|---|
| Talc | Balance |
| Synthetic mica | 6 |
| Plate-shaped alumina | 6 |

TABLE 12-continued

Loose powder (powder foundation)

|  | Example 48 |
|---|---|
| Red interference composite powder (Example 9) | 12 |
| Spherical nylon powder | 4 |
| Squalane | 3 |
| Paraben | q.s |
| Perfume | q.s |

TABLE 13

Powder foundation

|  | Example 49 |
|---|---|
| Sericite | 17 |
| Synthetic mica | 10 |
| Talc | Balance |
| Red interference composite powder (Example 10) | 6 |
| Titanium oxide | 10 |
| Bengala | 0.8 |
| Yellow iron oxide | 2 |
| Black iron oxide | 0.1 |
| Zinc oxide | 2 |
| Silicone elastic powder | 2 |
| Dimethylpolysiloxane | 3 |
| Liquid paraffin | 5 |
| Petrolatum | 5 |
| Sorbitan sesquiisostearate | 1 |
| Paraben | q.s |
| Antioxidant | q.s |
| Perfume | q.s |

TABLE 14

W/O type emulsified beauty lotion

|  | Example 50 |
|---|---|
| Cyclomethicone | 30 |
| Dimethicone | 2 |
| Alkyl modified polyether silicone | 2 |
| Silicone resin | 0.2 |
| Antioxidant | q.s |
| Octyl methoxycinnamate | 2 |
| Vitamin E derivative (blood circulation accelerant) | 0.5 |
| Arbutin (whitening agent) | 1 |
| Retinol (anti-wrinkle agent) | 1 |
| Mica composite powder (Example 23) | 2 |
| Siliconized barium sulfate | 3 |
| Cation modified bentonite | 2 |
| Talc | 5 |
| Spherical PMMA resin powder | 5 |
| Ion-exchange water | Balance |
| Glycerin | 4 |
| Polyethylene glycol | 1 |
| Antiseptic | q.s |
| Stabilizer | q.s |
| Perfume | q.s |

TABLE 15

O/W type emulsified beauty lotion

|  | Example 51 |
|---|---|
| Ion-exchange water | Balance |
| Glycerin | 20 |
| 1,2-pentanediol | 3 |
| 1,3-butylene glycol | 1 |
| Liquid paraffin | 7.5 |
| Isostearic acid | 0.5 |
| Nicotinic acid derivative (blood circulation accelerant) | 0.5 |
| Bramble extract (blood circulation accelerant) | 0.7 |
| Ascorbic acid (whitening agent) | 0.2 |
| Matricaria extract (whitening agent) | 0.1 |
| Saxifragaceae extract (whitening agent) | 0.3 |
| Di (2-ethylhexyl) phthalate | 0.3 |
| Polyethylene powder | 4 |
| Teflon powder | 4 |
| Red interference composite powder (Example 30) | 1 |
| Stabilizer | q.s |
| Perfume | q.s |

Cosmetics of Tables 11-15 were all effective in correcting skin surface unevenness and imperfections in skin color, and it was also effective in rendering a natural finish with clearness. In addition, the feeling of touch upon application was smooth and light.

Composite Powder with Adhering Zinc Oxide

Composite powders with adhering zinc oxide according to the present invention were prepared under various conditions (Examples 52-67).

Example 52

50 g of red interference titanated mica, which used as a substrate and had a particle diameter of ca. 12 μm, was weighed into a 1000 ml separable round bottom flask. To this was added 400 ml of ion-exchanged water, and the mixture was mixed with stirring. Separately, a 100 ml aqueous solution containing 0.5 g of yellow iron oxide particles (1 weight % with respect to the titanated mica), which were used as seed particles and had a particle diameter of ca. 0.3 μm, was prepared by ultrasonic dispersion. The solution was added to the slurry of the above titanated mica, and the mixture was mixed with stirring. The temperature of the titanated mica slurry was adjusted to 60° C., and 150 ml of zinc chloride aqueous solution with a concentration of 184 mmol/L and 500 ml of sodium hydroxide aqueous solution with a concentration of 250 mmol/L were separately added to the slurry. As soon as the solutions were added, white zinc oxide was formed and deposited. The reaction was continued for 2 hours.

Figure 16:
FIG. 16 shows an SEM picture of surface of a composite powder of Example 52.

The reaction solution was cooled to room temperature, and the obtained solid product was allowed to precipitate, filtered, and washed. After the salt was removed, the product was dried at 120° C. for 12 hours. After the product was dried, it was powdered and sieved to obtain red interference white powder of Example 52. An SEM picture of its powder surface is shown in FIG. 16. The adherence rate of zinc oxide on the obtained powder was 45 weight % with respect to the titanated mica, which was a substrate.

Example 53-55

50 g of various interference titanated mica (Example 53: yellow interference, Example 54: green interference, Example 55: blue interference), which was used as a substrate and had a particle diameter of ca. 12 μm was weighed into a 1000 ml separable round bottom flask. To this was added 400 ml of ion-exchanged water, and the mixture was mixed with stirring. Separately, a 100 ml aqueous solution containing 0.5 g of yellow iron oxide particles (1 weight % with respect to the titanated mica), which were used as seed particles and had a particle diameter of ca. 0.3 μm, was prepared by ultrasonic dispersion. The solution was added to the slurry of the above titanated mica, and the mixture was mixed with stirring. The temperature of the titanated mica slurry was adjusted to 60° C., and 150 ml of zinc chloride aqueous solution with a concentration of 184 mmol/L and 500 ml of sodium hydroxide aqueous solution with a concentration of 250 mmol/L were separately added to the slurry. As soon as the solutions were added, white zinc oxide was formed and deposited. The reaction was continued for 2 hours.

Figure 17:
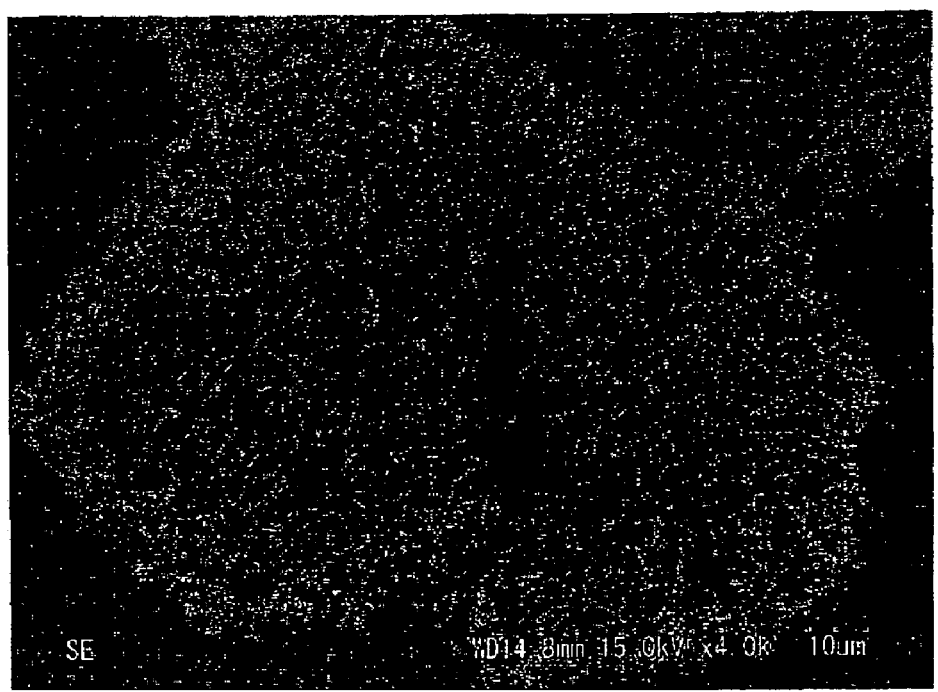
FIG. 17 shows an SEM picture of surface of a composite powder of Example 53.
Figure 18:
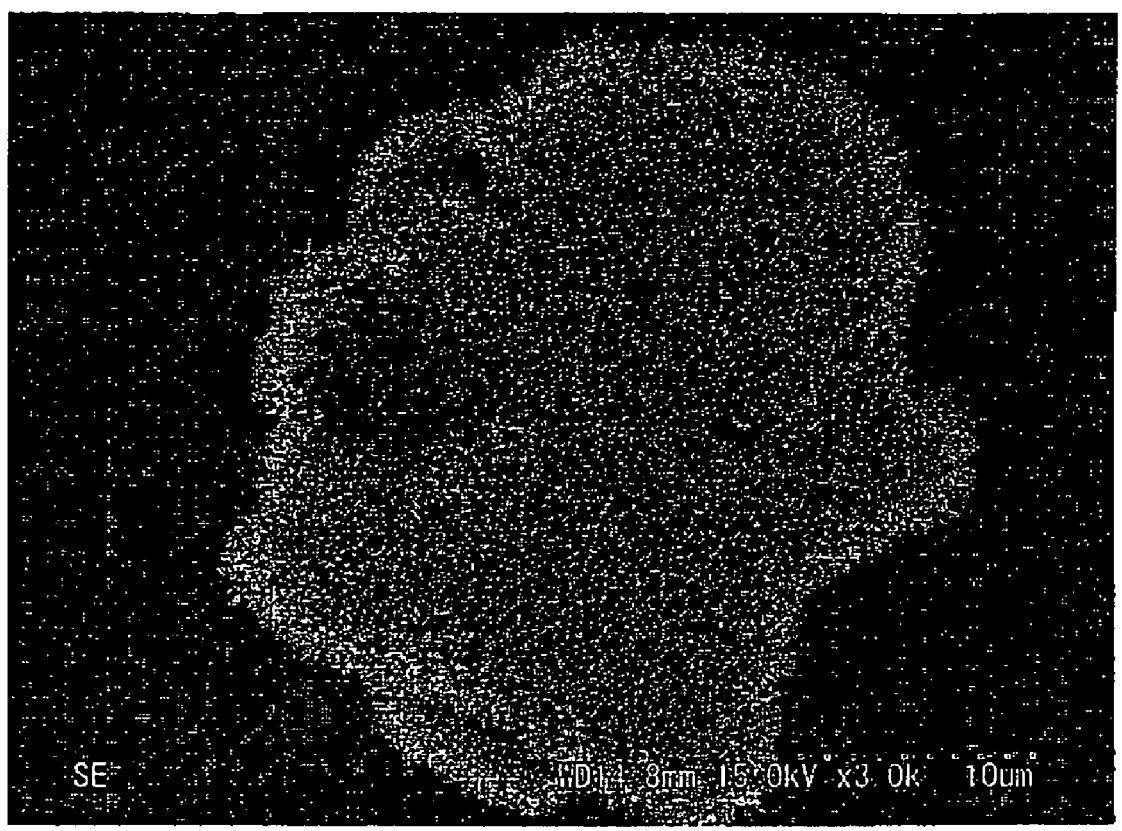
FIG. 18 shows an SEM picture of surface of a composite powder of Example 54.
Figure 19:
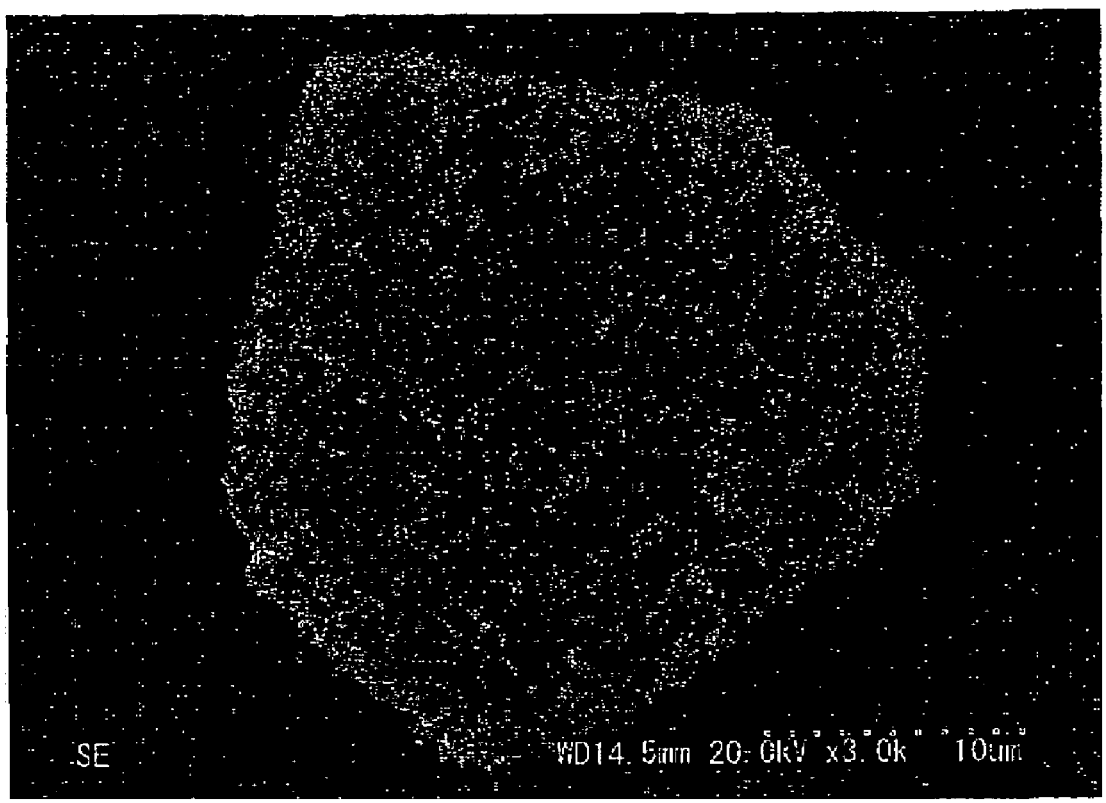
FIG. 19 shows an SEM picture of surface of a composite powder of Example 55.

The reaction solution was cooled to room temperature, and the obtained solid product was allowed to precipitate, filtered, and washed. After the salt was removed, the product was dried at 120° C. for 12 hours. After the product was dried, it was powdered and sieved to obtain various interference white powder of Examples 53-55 (Example 53: yellow interference, Example 54: green interference, Example 55: blue interference). SEM pictures of its powder surfaces are shown in FIG. 17-19. The adherence rate of zinc oxide on the obtained each powders were 100 weight % (Example 53), 30 weight % (Example 54), and 45 weight % (Example 55) with respect to the titanated mica, which was a substrate.

Example 56-59

50 g of various interference flaky powder (Timiron® sprendid (Merck), Example 56: red interference, Example 57: yellow interference, Example 58: green interference, Example 59: blue interference), which was used as a substrate and had a particle diameter of ca. 12 μm was weighed into a 1000 ml separable round bottom flask. To this was added 400 ml of ion-exchanged water, and the mixture was mixed with stirring. Separately, a 100 ml aqueous solution containing 0.5 g of yellow iron oxide particles (1 weight % with respect to the various interference flaky powder), which were used as seed particles and had a particle diameter of ca. 0.3 μm, was prepared by ultrasonic dispersion. The solution was added to the slurry of the above titanated mica, and the mixture was mixed with stirring. The temperature of the titanated mica slurry was adjusted to 60° C., and 150 ml of zinc chloride aqueous solution with a concentration of 184 mmol/L and 500 ml of sodium hydroxide aqueous solution with a concentration of 250 mmol/L were separately added to the slurry. As soon as the solutions were added, white zinc oxide was formed and deposited. The reaction was continued for 2 hours.

Figure 20:
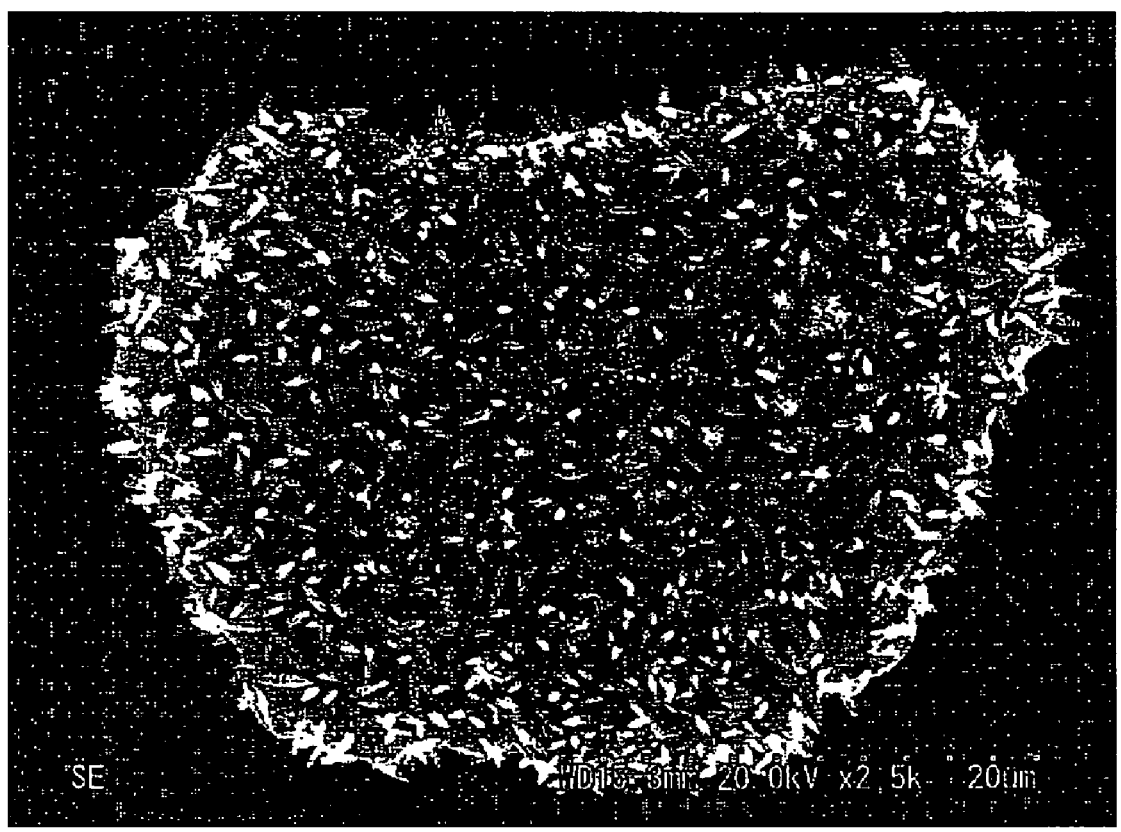
FIG. 20 shows an SEM picture of surface of a composite powder of Example 56.

The reaction solution was cooled to room temperature, and the obtained solid product was allowed to precipitate, filtered, and washed. After the salt was removed, the product was dried at 120° C. for 12 hours. After the product was dried, it was powdered and sieved to obtain various interference white powders of Examples 56-59 (Example 56: red interference, Example 57: yellow interference, Example 58: green interference, Example 59: blue interference). An SEM picture of powder surface of Example 56 is shown in FIG. 20. The adherence rate of zinc oxide on the obtained powder was 45 weight % with respect to the titanated mica, which was a substrate.

Example 60-62

50 g of red interference titanated mica, which used as a substrate and had a particle diameter of ca. 12 μm, was weighed into a 1000 ml separable round bottom flask. To this was added 400 ml of ion-exchanged water, and the mixture was mixed with stirring. Separately, a 100 ml aqueous solution containing 0.5 g of yellow iron oxide particles (1 weight % with respect to the titanated mica), which were used as seed particles and had a particle diameter of ca. 0.3 μm, was prepared by ultrasonic dispersion. The solution was added to the slurry of the above titanated mica, and the mixture was mixed with stirring. Furthermore, for coexisting of various acid (Example 60: glutamic acid, Example 61: acetic acid, Example 62: asparagic acid) with an amount of 1 equivalent with respect to zinc ion, glutamic acid in Example 60, acetic acid in Example 61, and asparagic acid in Example 62 were added respectively. The temperature of the titanated mica slurry was adjusted to 60° C., and 150 ml of zinc chloride aqueous solution with a concentration of 184 mmol/L and 500 ml of sodium hydroxide aqueous solution with a concentration of 250 mmol/L were separately added to the slurry. As soon as the solutions were added, white zinc oxide was formed and deposited. The reaction was continued for 2 hours.

Figure 21:
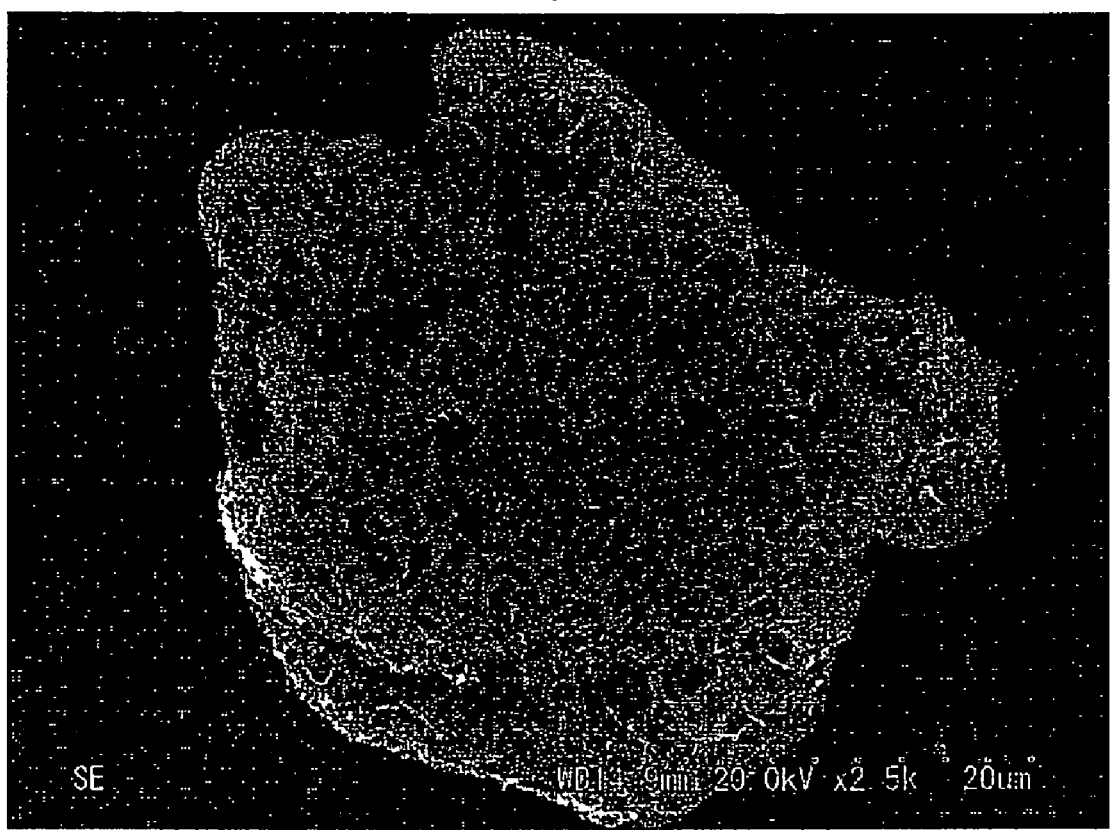
FIG. 21 shows an SEM picture of surface of a composite powder of Example 60.
Figure 22:
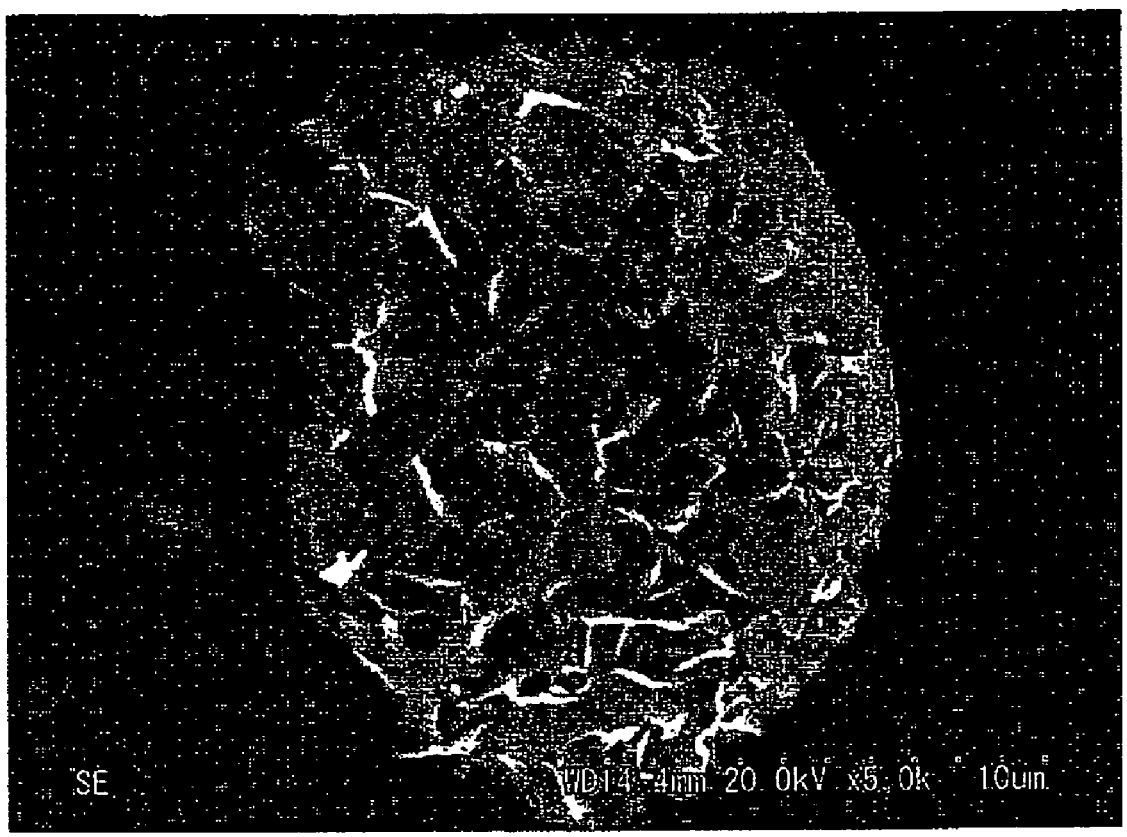
FIG. 22 shows an SEM picture of surface of a composite powder of Example 61.
Figure 23:
FIG. 23 shows an SEM picture of surface of a composite powder of Example 62.

The reaction solution was cooled to room temperature, and the obtained solid product was allowed to precipitate, filtered, and washed. After the salt was removed, the product was dried at 120° C. for 12 hours. After the product was dried, it was powdered and sieved to obtain red interference white powder of Examples 60-62. SEM pictures of its powder surfaces are shown in FIG. 21-23. The adherence rate of zinc oxide on the obtained powder was 45 weight % with respect to the titanated mica, which was a substrate.

Example 63-64

50 g of red interference titanated mica, which used as a substrate and had a particle diameter of ca. 12 μm, was weighed into a 1000 ml separable round bottom flask. To this was added 400 ml of ion-exchanged water, and the mixture was mixed with stirring. Separately, a 100 ml aqueous solution containing 0.5 g of yellow iron oxide particles (1 weight % with respect to the titanated mica), which were used as seed particles and had a particle diameter of ca. 0.3 μm, was prepared by ultrasonic dispersion. The solution was added to the slurry of the above titanated mica, and the mixture was mixed with stirring. Furthermore, various metal ions (Example 63: magnesium ion, Example 64: calcium ion) were added for coexisting each metal ion with an amount of 1 equivalent with respect to zinc ion. The temperature of the titanated mica slurry was adjusted to 60° C., and 150 ml of zinc chloride aqueous solution with a concentration of 184 mmol/L and 500 ml of sodium hydroxide aqueous solution with a concentration of 250 mmol/L were separately added to the slurry. As soon as the solutions were added, white zinc oxide was formed and deposited. The reaction was continued for 2 hours.

The reaction solution was cooled to room temperature, and the obtained solid product was allowed to precipitate, filtered, and washed. After the salt was removed, the product was dried at 120° C. for 12 hours. After the product was dried, it was powdered and sieved to obtain red interference white powder of Examples 63-64. The amount of zinc oxide on the obtained powder was 45 weight % with respect to the titanated mica, which was a substrate.

Example 65-67

50 g of talc (Example 65), or mica (Example 66, 67), used as a substrate, with a particle diameter of ca. 12 μm was weighed into a 1000 ml separable round bottom flask. To this was added 400 ml of ion-exchanged water, and the mixture was mixed with stirring. Separately, a 100 ml aqueous solution containing 0.5 g of yellow iron oxide particles (1 weight % with respect to the talc or mica), which were used as seed particles and had a particle diameter of ca. 0.3 μm, was prepared by ultrasonic dispersion. The solution was added to the slurry of the above titanated mica, and the mixture was mixed with stirring. The temperature of the titanated mica slurry was adjusted to 60° C., and 150 ml of zinc chloride aqueous solution with a concentration of 184 mmol/L and 500 ml of sodium hydroxide aqueous solution with a concentration of 250 mmol/L were separately added to the slurry. As soon as the solutions were added, white zinc oxide was formed and deposited. The reaction was continued for 2 hours.

Figure 24:
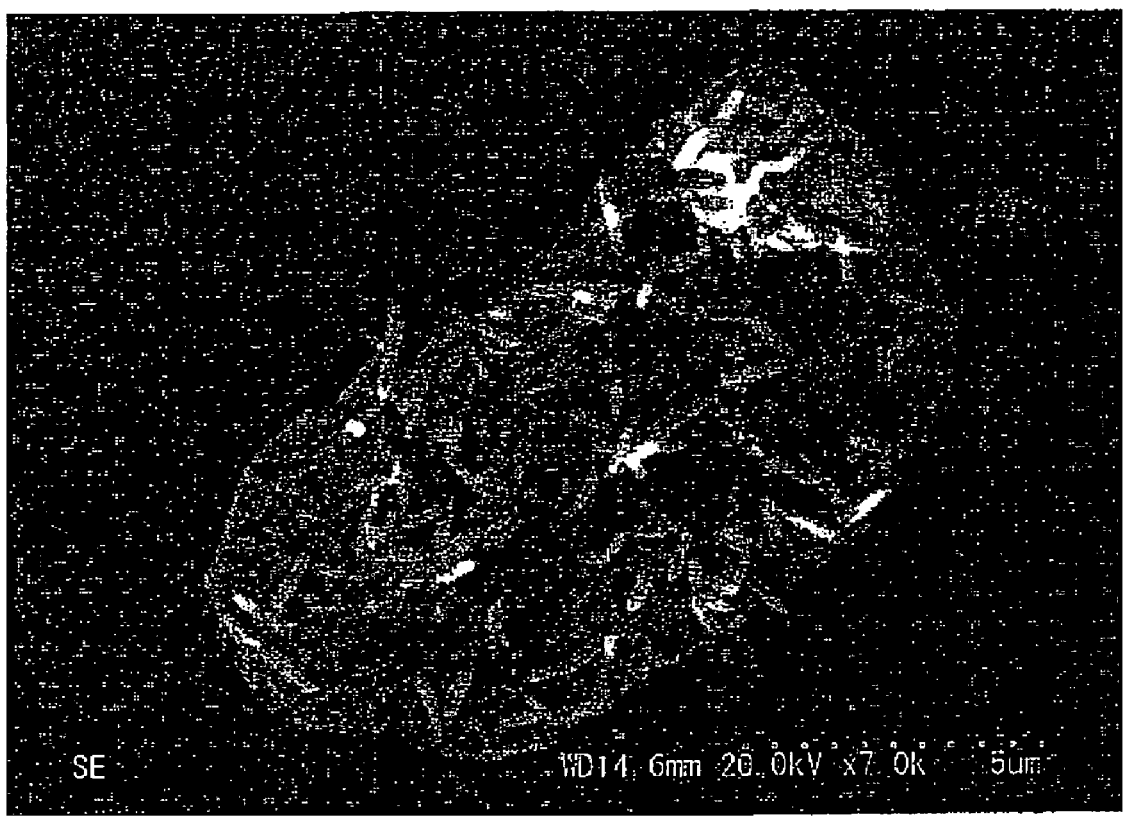
FIG. 24 shows an SEM picture of surface of a composite powder of Example 65.
Figure 25:
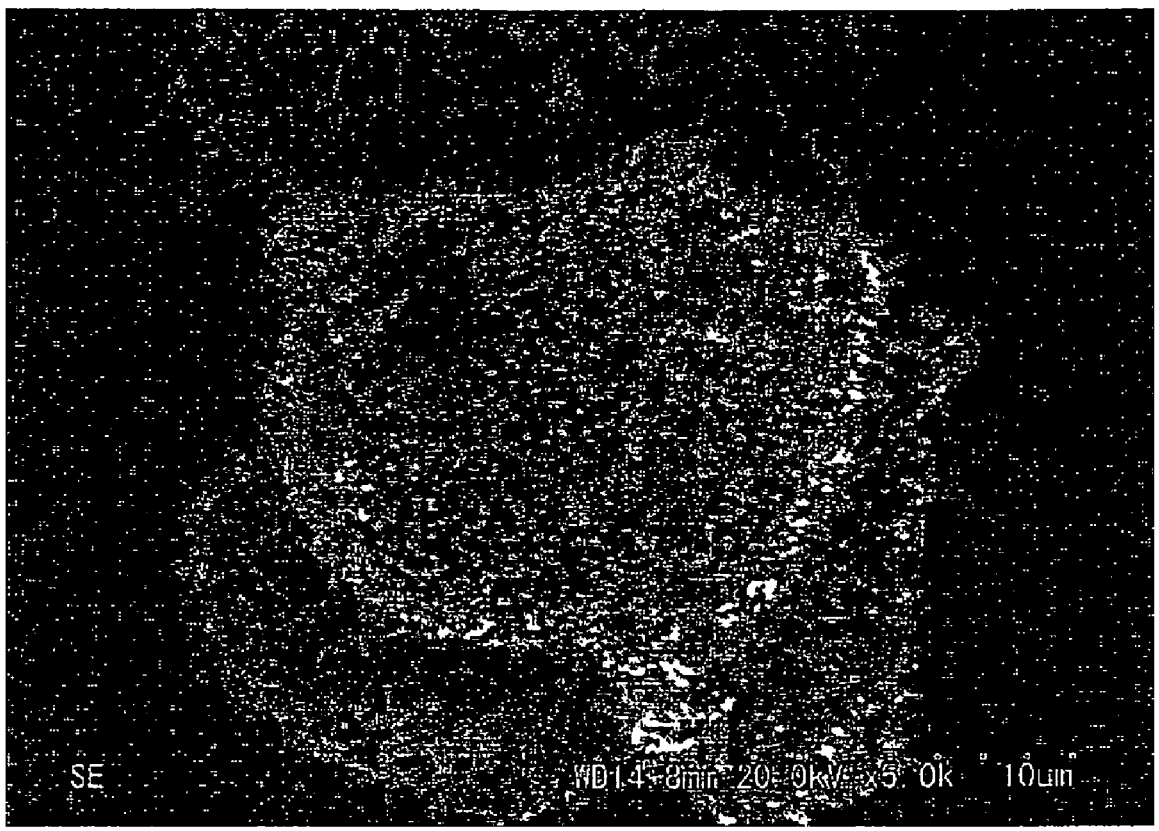
FIG. 25 shows an SEM picture of surface of a composite powder of Example 66.
Figure 26:
FIG. 26 shows an SEM picture of surface of a composite powder of Example 67.

The reaction solution was cooled to room temperature, and the obtained solid product was allowed to precipitate, filtered, and washed. After the salt was removed, the product was dried at 120° C. for 12 hours. After the product was dried, it was powdered and sieved to obtain red interference white powder of Examples 65-67. SEM pictures of its powder surfaces are shown in FIG. 24-26.

Comparative Example 20

As a Comparative Example, a white powder was obtained by a similar preparation method to that of Example 52 except for the adding no seed particles, and the adjustment of a suitable amount of ion-exchanged water.

Various cosmetics in which composite powders of the above examples were blended were evaluated. The cosmetics were applied to 20 female panel members, and the application characteristics such as effectiveness in correcting skin surface unevenness (pores, fine wrinkles, etc. of the skin) and imperfections in skin color (dullness, blotches, freckles, redness, dark rings around the eyes, etc.), clearness, natural finish, and undesirable gloss over time were evaluated based on the criteria described below.

Evaluation Criteria for Application Characteristics
◎ More than 16 persons answered "good".
○ 12-16 persons answered "good".
Δ 9-11 persons answered "good".
X 5-8 persons answered "good".
XX Less than 5 persons answered "good".

Formulations of cosmetics and their evaluation results are shown below.

TABLE 16

| Powder foundation | | | |
|---|---|---|---|
| | Example 68 | Comparative Example 21 | Comparative Example 22 |
| Sericite | 17 | 17 | 17 |
| Synthetic mica | 10 | 10 | 10 |
| Talc | Balance | Balance | Balance |
| Red interference composite powder (Example 52) | 8 | — | — |
| Composite powder (Comparative Example 20) | — | 8 | — |
| Red interference titanated mica | — | — | 8 |
| Titanium oxide | 10 | 10 | 10 |
| Bengala | 0.8 | 0.8 | 0.8 |
| Yellow iron oxide | 2 | 2 | 2 |
| Black iron oxide | 0.1 | 0.1 | 0.1 |
| Zinc oxide | 2 | 2 | 2 |
| Silicone elastic powder | 2 | 2 | 2 |
| Dimethylpolysiloxane | 3 | 3 | 3 |
| Liquid paraffin | 5 | 5 | 5 |
| Petrolatum | 5 | 5 | 5 |
| Sorbitan sesquiisostearate | 1 | 1 | 1 |
| Paraben | q.s | q.s | q.s |
| Antioxidant | q.s | q.s | q.s |
| Perfume | q.s | q.s | q.s |
| Correction effect for skin unevenness | ◎ | ○ | X |
| Correction effect for skin dullness | ◎ | Δ | ○ |
| Clearness of finished makeup | ◎ | Δ | Δ |
| Naturality of finished makeup | ○ | Δ | X |
| Undesirable gloss caused over time | ◎ | Δ | XX |

As is clear from Table 16, the foundation of Example 68 containing the composite powder of Example 52 was effective in correcting skin surface unevenness and imperfections in skin color, and it was also effective in rendering a natural finish with clearness. In addition, an undesirable gloss caused over time due to sebum was suppressed.

On the other hand, the foundation of Comparative Example 21 containing the composite powder of Comparative Example 20 was not effective in correcting skin surface unevenness and imperfections in skin color, and it was also not effective in rendering a natural finish with clearness. In addition, an undesirable gloss was caused over time. The foundation of Comparative Example 22 containing interference titanated mica could correct imperfections in skin color. However, skin surface unevenness was conspicuous, there was a glare, and a natural finish with clearness could not be achieved. In addition, an undesirable gloss was caused over time.

TABLE 17

| Powder foundation (summer powder cake-type foundation allowing water use) | | | |
|---|---|---|---|
| | Example 69 | Comparative Example 23 | Comparative Example 24 |
| Siliconized sericite | 18 | 18 | 18 |
| Siliconized mica | Balance | Balance | Balance |
| Siliconized talc | 15 | 15 | 15 |
| Siliconized yellow interference composite powder (Example 53) | 8 | — | — |
| Siliconized composite powder (Comparative Example 20) | — | 8 | — |
| Siliconized yellow interference titanated mica | — | — | 8 |
| Siliconized titanium oxide | 8 | 8 | 8 |
| Aluminum stearate treated fine particle titanium oxide | 6 | 6 | 6 |
| Siliconized bengala | 1.2 | 1.2 | 1.2 |
| Siliconized yellow iron oxide | 2.5 | 2.5 | 2.5 |
| Siliconized black iron oxide | 0.9 | 0.9 | 0.9 |
| Polyurethane powder | 2 | 2 | 2 |

TABLE 17-continued

Powder foundation (summer powder cake-type foundation allowing water use)

| | Example 69 | Comparative Example 23 | Comparative Example 24 |
|---|---|---|---|
| Paraben | q.s | q.s | q.s |
| Dimethylpolysiloxane | 4 | 4 | 4 |
| Methylphenylpolysiloxane | 3 | 3 | 3 |
| Octyl methoxycinnamate | 3 | 3 | 3 |
| Polyether modified silicone | 2 | 2 | 2 |
| Antioxidant | q.s | q.s | q.s |
| Perfume | q.s | q.s | q.s |
| Correction effect for skin unevenness | ○ | X | XX |
| Correction effect for skin blotches and freckles | ◎ | Δ | Δ |
| Clearness of finished makeup | ◎ | Δ | X |
| Naturality of finished makeup | ○ | Δ | X |
| Undesirable gloss caused over time | ◎ | X | XX |

As is clear from Table 17, the foundation of Example 69 containing the composite powder of Example 53 was effective in correcting skin surface unevenness and imperfections in skin color, and it was also effective in rendering a natural finish with clearness. In addition, an undesirable gloss caused over time due to sebum was suppressed.

On the other hand, the foundation of Comparative Example 23 containing the composite powder of Comparative Example 20 was not effective in correcting skin surface unevenness, and it was also not effective in rendering clearness and a natural finish. In addition, an undesirable gloss was caused over time. With the foundation of Comparative Example 24 containing interference titanated mica, skin surface unevenness was conspicuous, there was a glare, and a natural finish with clearness could not be achieved. In addition, an undesirable gloss was caused over time.

TABLE 18

Face powder

| | Example 70 | Example 71 | Comparative Example 25 |
|---|---|---|---|
| Talc | Balance | Balance | Balance |
| Mica | 20 | 20 | 20 |
| Plate-shaped zinc oxide | 5 | 5 | 5 |
| Red interference composite powder (Example 52) | 4 | — | — |
| Red interference composite powder (Example 56) | — | 4 | — |
| Red interference titanated mica | — | — | 4 |
| Fine particle titanium oxide | 3 | 3 | 3 |
| Spherical silicone powder | 3 | 3 | 3 |
| Petrolatum | 1 | 1 | 1 |
| Squalane | 3 | 3 | 3 |
| Ester oil | 1 | 1 | 1 |
| Paraben | q.s | q.s | q.s |
| Antioxidant | q.s | q.s | q.s |
| Perfume | q.s | q.s | q.s |
| Correction effect for skin unevenness | ○ | ○ | X |
| Correction effect for skin dullness | ○ | ◎ | Δ |
| Clearness of finished makeup | ○ | ○ | Δ |
| Naturality of finished makeup | ○ | ◎ | X |
| Undesirable gloss caused over time | ◎ | ○ | X |

As is clear from Table 18, the face powders of Examples 70 and 71 containing the composite powders of Examples 52 and 56, respectively, were effective in correcting skin surface unevenness and imperfections in skin color, and they were also effective in rendering a natural finish with clearness. In addition, the feeling of touch upon application was smooth and light. Furthermore, an undesirable gloss caused over time due to sebum was suppressed.

On the other hand, with the face powders of Comparative Example 25 containing red interference titanated mica, skin surface unevenness was conspicuous, there was a glare, and a natural finish with clearness could not be achieved. In addition, an undesirable gloss was caused over time.

TABLE 19

Powder foundation (summer powder cake-type foundation allowing water use)

| | Example 72 | Example 73 | Comparative Example 26 |
|---|---|---|---|
| Siliconized mica | 25 | 25 | 25 |
| Siliconized sericite | 17 | 17 | 17 |
| Siliconized talc | Balance | Balance | Balance |
| Siliconized red interference composite powder (Example 62) | 12 | — | — |
| Siliconized red interference composite powder (Example 52) | — | 12 | — |
| Siliconized red interference titanated mica | — | — | 12 |
| Siliconized titanium oxide | 10 | 10 | 10 |
| Spherical PMMA powder | 4 | 4 | 4 |
| Paraben | q.s | q.s | q.s |
| Dimethylpolysiloxane | 4 | 4 | 4 |
| Methylphenylpolysiloxane | 1 | 1 | 1 |
| Petrolatum | 3 | 3 | 3 |
| Octyl methoxycinnamate | 3 | 3 | 3 |
| Sorbitan diisostearate | 1 | 1 | 1 |
| Antioxidant | q.s | q.s | q.s |
| Perfume | q.s | q.s | q.s |
| Correction effect for skin unevenness | ◎ | ○ | XX |
| Correction effect for skin dullness | ◎ | ○ | Δ |
| Clearness of finished makeup | ◎ | ○ | X |
| Narurality of finished makeup | ○ | ○ | X |
| Undesirable gloss caused over time | ○ | ○ | XX |

As is clear from Table 19, the foundations of Examples 72 and 73 containing the composite powders of Examples 52 and 62, respectively, were effective in correcting skin surface unevenness and imperfections in skin color, and they were also effective in rendering a natural finish with clearness. In addition, the feeling of touch upon application was smooth and light. Furthermore, an undesirable gloss caused over time due to sebum was suppressed.

On the other hand, with the foundations of Comparative Example 26 containing interference titanated mica, skin surface unevenness was conspicuous, there was a glare, and a natural finish with clearness could not be achieved. In addition, an undesirable gloss was caused over time.

Formulations of other examples are shown below.

TABLE 20

O/W type emulsified cream foundation

| | Example 74 |
|---|---|
| Talc | 8 |
| Sericite | 7 |
| Red interference composite powder (Example 55) | 6 |
| Titanium oxide | 10 |

TABLE 20-continued

O/W type emulsified cream foundation

|  | Example 74 |
|---|---|
| Bengala | 0.3 |
| Yellow iron oxide | 1.2 |
| Black iron oxide | 0.6 |
| Spherical polyethylene powder | 6 |
| Squalane | 10 |
| Olive oil | 10 |
| Stearic acid | 2 |
| Glyceryl monostearate | 2 |
| Sorbitan POE(40) monostearate | 2 |
| Glycerin | 5 |
| Triethanolamine | 0.8 |
| pH adjuster | q.s |
| Preservative | q.s |
| Ion-exchange water | Balance |

TABLE 21

Loose powder (face powder)

|  | Example 75 |
|---|---|
| Talc | Balance |
| Synthetic mica | 6 |
| Plate-shaped alumina | 6 |
| Red interference composite powder (Example 55) | 20 |
| Spherical nylon powder | 4 |
| Squalane | 3 |
| Paraben | q.s |
| Perfume | q.s |

TABLE 22

Powder foundation

|  | Example 76 |
|---|---|
| Sericite | 17 |
| Synthetic mica | 10 |
| Talc | Balance |
| Red interference composite powder (Example 58) | 6 |
| Titanium oxide | 10 |
| Bengala | 0.8 |
| Yellow iron oxide | 2 |
| Black iron oxide | 0.1 |
| Zinc oxide | 2 |
| Silicone elastic powder | 2 |
| Dimethylpolysiloxane | 3 |
| Liquid paraffin | 5 |
| Petrolatum | 5 |
| Sorbitan sesquiisostearate | 1 |
| Paraben | q.s |
| Antioxidant | q.s |
| Perfume | q.s |

All of the cosmetics in Tables 20-22 were very effective in correcting skin surface unevenness and imperfections in skin color, and they were also effective in rendering a natural finish with clearness. In addition, an undesirable gloss caused over time due to sebum was suppressed.

In the sections below, optical characteristics (glare) and the sebum solidifying effect were measured and evaluated for the composite powders that were prepared by the following methods.

Examples 77-79

50 g of red interference titanated mica, which was used as a substrate and had a particle diameter of ca. 12 μm, was weighed into a 1000 ml separable round bottom flask. To this was added 400 ml of ion-exchanged water, and the mixture was mixed with stirring. Separately, a 100 ml aqueous solution containing yellow iron oxide particles (1 weight % (Example 77), 3 weight % (Example 78), or 5 weight % (Example 79) with respect to the titanated mica), which were used as seed particles and had a particle diameter of ca. 0.3 μm, was prepared by ultrasonic dispersion. The solution was added to the slurry of the above titanated mica, and the mixture was mixed with stirring. The temperature of the titanated mica slurry was adjusted to 60° C. The zinc chloride aqueous solution and the sodium hydroxide aqueous solution were separately added to the slurry so that the adherence rate of zinc oxide with respect to the substrate is 30% (Example 77), 50% (Example 78) or 100% (Example 79). As soon as the solutions were added, white zinc oxide was formed and deposited. The reaction was continued for 30 minutes.

The reaction solution was cooled to room temperature, and the obtained solid product was allowed to precipitate, was filtered, and was washed. After the salt was removed, the product was dried at 150° C. for 12 hours. After the product was dried, it was powdered and sieved to obtain red interference white powder of Examples 77-79.

Comparative Example 27

A white powder of Comparative Example 27 was obtained by a similar preparation method to the above except for the addition no seed particles, and for that the adhesion rate of zinc oxide was set at 15% with respect to the substrate.

Measurement and Evaluation of Glare

Figure 27:
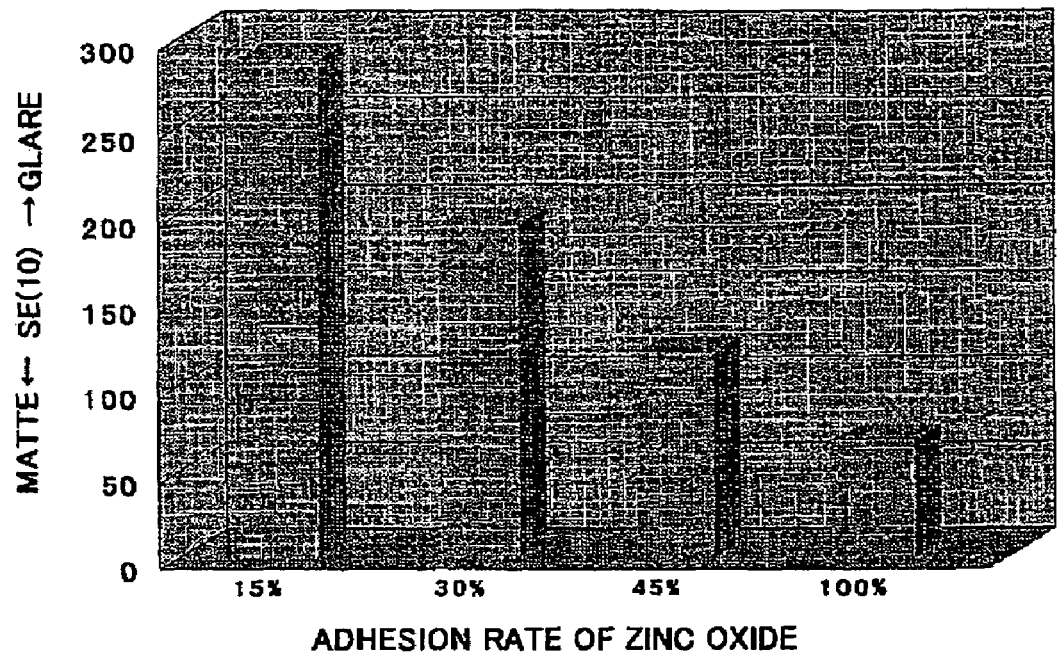
FIG. 27 shows a graph for evaluation of undesirable glare of powder by SE value measured by microglarimeter.

The SE value was measured with a microglarimeter to evaluate the glare for the composite powders of Examples 77-79 and the powder of Comparative Example 27, and the results are shown in FIG. 27.

As is clear from FIG. 27, the glare is reduced for the powders of Examples 77-79, which were prepared with seed particles, compared with the powder of Comparative Example 27, which was prepared without seed particles.

Measurement and Evaluation of Sebum-Solidifying Effect

The hardness was measured with a rheometer to evaluate the sebum-solidifying effect of the composite powders of Examples 77-79, the composite powder of Comparative Example 27, and red interference titanated mica (Timiron® Super Red) and zinc oxide (AZO-BS), which are not composited. The results are shown in FIG. 28.

Figure 28:
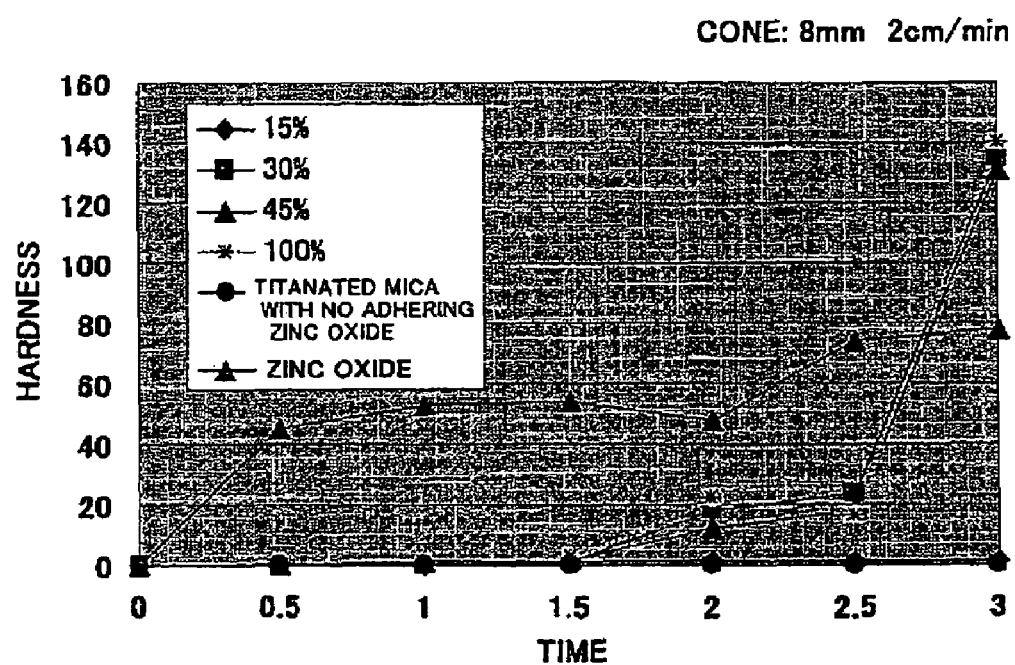
FIG. 28 shows a plot for evaluation of sebum-solidifying effect of powder by hardness measured by rheometer.

As is clear from FIG. 28, the powders of Examples 77-79 solidify sebum over time while the powder of Comparative Example 27 and the interference titanated mica do not. Even when compared with zinc oxide, the powders of Examples 77-79 achieve an excellent sebum-solidifying effect over time. Thus, the powders of Examples 77-79 have an especially excellent sebum-solidifying effect over time. Accordingly, if these powders are blended in makeup cosmetics, the cosmetics can effectively suppress an undesirable gloss and makeup deterioration due to sebum secretion, which takes place over time, and it can achieve a long-lasting finish.

What is claimed is:

1. A composite powder comprising:
   a) a flaky substrate powder,
   b) seed particles selected from the group consisting of titanium oxide, zinc oxide, alumina, aluminum hydroxide, silica, iron oxide; and
   c) barium sulfate particles or zinc oxide particles;
   wherein
   i) the seed particles act as nuclei on the surface of the flaky substrate powder and the barium sulfate particles or the zinc oxide particles adhere to the flaky substrate powder particles through the seed particles, and
   ii) the coverage with barium sulfate particles is 10-70% with respect to the surface area of said substrate powder or the coverage with zinc oxide particles is 40-90% with respect to the surface area of said substrate powder.

2. The composite powder according to claim 1, wherein said substrate powder generates interference colors.

3. The composite powder according to claim 2, wherein said substrate powder is titanated mica.

4. The composite powder according to claim 3, wherein barium sulfate particles or zinc oxide particles, which adhere to the surface of said substrate powder, have approximately uniform particle diameters.

5. The composite powder according to claim 4, wherein said barium sulfate particles or zinc oxide particles adhere to the surface of said substrate powder so that the distance between the particles is approximately uniform.

6. The composite powder according to claim 1, wherein the adhesion rate of barium sulfate particles or zinc oxide particles to said substrate is 15-100 weight %.

7. The composite powder according to claim 1, wherein particles adhering to the surface of said substrate are barium sulfate particles.

8. The composite powder according to claim 7, wherein said barium sulfate particles are flaky, and said barium sulfate particles adhere to the surface of the substrate powder by contacting at the peripheral points of the flakes and adhere at a certain angle with respect to the surface of the substrate powder.

9. The composite powder according to claim 8, wherein said barium sulfate particles are approximately square flakes, and said barium sulfate particles adhere to the surface of the substrate powder by contacting at the peripheral points of the flakes and adhere at a certain angle with respect to the surface of the substrate powder.

10. The composite powder according to claim 7, wherein said barium sulfate particles are spherical, and the number average particle diameter of said particles is 0.5-5.0 μm.

11. The composite powder according to claim 1, wherein particles adhering to the surface of said substrate are zinc oxide particles.

12. The composite powder according to claim 11, wherein said zinc oxide particles are long needle-shape.

13. A cosmetic comprising a composite powder according to claim 1.

14. A method of producing a composite powder comprising a flaky substrate powder, seed particles and adhering barium sulfate particles comprising the steps of:
   a) preparing a slurry solution of a flaky substrate powder,
   b) separately preparing a solution of seed particles,
   c) adding the solution of seed particles to the slurry solution of the flaky substrate powder,
   d) separately preparing a barium ion solution,
   e) separately preparing a sulfate ion solution,
   f) adding the barium ion solution and the sulfate ion solution separately to the slurry solution comprising seed particles and the flaky substrate powder,
   g) allowing the barium ion solution and the sulfate ion solution to react and form barium sulfate particles;
   wherein
   i) the seed particles act as nuclei, and
   ii) the barium sulfate particles adhere to the flaky substrate powder particles through the seed particles.

15. A method of producing a composite powder comprising a flaky substrate powder, seed particles and adhering zinc oxide particles comprising the steps of:
   a) preparing a slurry solution of a flaky substrate powder,
   b) separately preparing a solution of seed particles,
   c) adding the solution of seed particles to the slurry solution of the flaky substrate powder,
   d) separately preparing a zinc ion solution,
   e) separately preparing an alkali aqueous solution,
   f) adding the zinc ion solution and the alkali aqueous solution separately to the slurry solution comprising seed particles and the flaky substrate powder,
   g) allowing the zinc ion solution and the alkali aqueous solution to react and form zinc oxide particles;
   wherein
   i) the seed particles act as nuclei, and
   ii) the zinc oxide particles adhere to the flaky substrate powder particles through the seed particles.

16. The method of producing composite powder according to claim 14 wherein the amount of the added seed particles is 0.1-15 weight % with respect to that of the substrate powder.

17. The method of producing composite powder according to claim 14 wherein the reaction is conducted under the conditions that the pH of the slurry solution is always adjusted in a range of 7-9.

18. The method of producing composite powder adhering barium sulfate particles according to claim 14, wherein one or more complexing agents is allowed to coexist in the slurry solution.

19. The method of producing composite powder containing adhering barium sulfate particles according to claim 18, wherein the amount of added complexing agent is 0.4-10.0 equivalents with respect to that of the barium.

20. The composite powder of claim 1 further comprising seed particles, wherein the barium sulfate particles or zinc oxide adhere to the substrate particles through said seed particles.

* * * * *